United States Patent
Darling et al.

(10) Patent No.: US 11,772,061 B2
(45) Date of Patent: Oct. 3, 2023

(54) METHODS OF FABRICATING HYPER COMPLIANT POLYMER PARTICLES AND METHODS OF USE AND COMPOSITIONS

(71) Applicant: Brown University, Providence, RI (US)

(72) Inventors: Eric M. Darling, Norfolk, MA (US); Nicholas R. Labriola, Farmington, NY (US); Edith Mathiowitz, Brookline, MA (US)

(73) Assignee: Brown University, Providence, RI (US)

( * ) Notice: Subject to any disclaimer, the term of this patent is extended or adjusted under 35 U.S.C. 154(b) by 463 days.

(21) Appl. No.: 16/465,374

(22) PCT Filed: Nov. 30, 2017

(86) PCT No.: PCT/US2017/063825
§ 371 (c)(1),
(2) Date: May 30, 2019

(87) PCT Pub. No.: WO2018/102480
PCT Pub. Date: Jun. 7, 2018

(65) Prior Publication Data
US 2019/0329210 A1    Oct. 31, 2019

Related U.S. Application Data

(60) Provisional application No. 62/520,066, filed on Jun. 15, 2017, provisional application No. 62/428,029, filed on Nov. 30, 2016.

(51) Int. Cl.
| | |
|---|---|
| *A61K 9/50* | (2006.01) |
| *A61K 9/51* | (2006.01) |
| *A61K 9/00* | (2006.01) |
| *A61K 9/16* | (2006.01) |
| *B01J 13/14* | (2006.01) |
| *B01J 13/22* | (2006.01) |
| *B01L 3/00* | (2006.01) |

(52) U.S. Cl.
CPC .............. *B01J 13/14* (2013.01); *A61K 9/5021* (2013.01); *A61K 9/5073* (2013.01); *A61K 9/5089* (2013.01); *A61K 9/5138* (2013.01); *B01J 13/22* (2013.01); *B01L 3/50273* (2013.01); *B01L 2200/148* (2013.01)

(58) Field of Classification Search
CPC ......... B01J 13/14; B01J 13/22; A61K 9/5021; A61K 9/5073; A61K 9/5089; A61K 9/5138; B01L 3/50273; B01L 2200/148
See application file for complete search history.

(56) References Cited

U.S. PATENT DOCUMENTS

| | | |
|---|---|---|
| 2005/0175702 A1 | 8/2005 | Muller-Schulte |
| 2009/0022808 A1 | 1/2009 | Champion et al. |
| 2015/0367035 A1 | 12/2015 | Kumaraswamy et al. |
| 2016/0008291 A1 | 1/2016 | Ischakov et al. |
| 2016/0299051 A1 | 10/2016 | Kim et al. |
| 2016/0318001 A1 | 11/2016 | Subramanyam et al. |

FOREIGN PATENT DOCUMENTS

| | | |
|---|---|---|
| CN | 102382226 A | 3/2012 |
| WO | 2013125279 A1 | 8/2013 |
| WO | 2014/207304 A1 * | 12/2014 |
| WO | 2016/004068 A1 * | 1/2017 |

OTHER PUBLICATIONS

Martin (Phys. Chem. Chem. Phys., pp. 3014-3018, published Dec. 23, 2014, Supporting Information pp. 1-10) (Year: 2014).*
Desai et al. (Biomaterials, pp. 30-37, published 2015). (Year: 2015).*
PCT/US2017/063825 International Search Report and Written Opinion, dated Mar. 19, 2018.
Anslemo, AC , et al., "Elasticity of nanoparticles influences their blood circulation, phagocytosis, endocytosis, and targeting.", ACS nano, vol. 9, No. 3, Mar. 4, 2015, 3169-3177.
Martin, S , et al., "Quantification of protein-materials interaction by soft colloidal probe spectroscopy.", Physical Chemistry Chemical Physics, vol. 17, No. 5, 2015, 3014-3018.
Hur et al., "Deformability-Based Cell Classification and Enrichment Using Inertial Microfluidics", Lab on a Chip, vol. 11, 2011, pp. 912-920.
Hur et al., "Label-Free Enrichment of Adrenal Cortical Progenitor Cells Using Inertial Microfluidics", Plos One, vol. 7, Issue 10, e46550, Oct. 4, 2012, pp. 1-7.

(Continued)

*Primary Examiner* — Alma Pipic
(74) *Attorney, Agent, or Firm* — Adler Pollock & Sheehan P.C.

(57) ABSTRACT

Compositions and methods are provided for making hyper compliant polymer particles by inverse emulsification and having a predetermined mechanical compliance and a predetermined size with a monodisperse diameter. Compositions and methods are provided for use of hyper compliant polymer particles in drug delivery, assay, particle image velocimetry, ceramics, cosmetics, deconvolution, electronic paper, insulation, personal care, standards, retroreflective paint and paint applications, thickening agents, regenerative medicine, device calibration, micro-carriers and force indicators.

5 Claims, 14 Drawing Sheets

(56) References Cited

OTHER PUBLICATIONS

Jiang et al., "Aerosol-Assisted Self-Assembly of Single-Crystal Core/Nanoporous Shell Particles as Model Controlled Release Capsules", J. Am. Chem. Soc., vol. 128, No. 14, Mar. 16, 2006, pp. 4512-4513.
Juliano et al., "The Effect of Particle Size and Charge on the Clearance Rates of Liposomes and Liposome Encapsulated Drugs", Biochemical and Biophysical Research Communications, vol. 63, Issue 3, Apr. 7, 1975, pp. 651-658.
Kaehr et al., "Cellular Complexity Captured in Durable Silica Biocomposites", Proc. Natl. Acad. Sci., vol. 109, No. 43, Oct. 23, 2012, pp. 17336-17341.
Kamaly et al., "Targeted Polymeric Therapeutic Nanoparticles: Design, Development and Clinical Translation", Chem. Soc. Rev., vol. 41, No. 7, Apr. 7, 2012, pp. 2971-3010.
Kanthilal et al., "Characterization of Mechanical and Regenerative Properties of Human, Adipose Stromal Cells", Cellular and Molecular Bio-engineering, vol. 7, No. 4, Dec. 1, 2014, pp. 585-597.
Kilian et al., "Geometric Cues for Directing the Differentiation of Mesenchymal Stem Cells", PNAS, vol. 107, No. 11, Mar. 16, 2010, pp. 4872-4877.
Kiser et al., "A Synthetic Mimic of the Secretory Granule for Drug Delivery", Nature, vol. 394, Jul. 30, 1998, pp. 459-462.
Kozlovskaya et al., "Internalization of Red Blood Cell-Mimicking Hydrogel Capsules with pH-Triggered Shape Responses", ACS Nano, vol. 8, No. 6, 2014, pp. 5725-5737.
Kronberg et al., "Surface Chemistry of Surfactants and Polymers", Wiley, Dec. 2014, 496 pages.
Kumachev et al., "High-Throughput Generation of Hydrogel Microbeads With Varying Elasticity for Cell Encapsulation", Biomaterials, vol. 32, Issue 6, Feb. 2011, pp. 1477-1483.
Kumari et al., "Biodegradable Polymeric Nanoparticles Based Drug Delivery Systems", Colloids and Surfaces B: Biointerfaces, vol. 75, Issue 1, Jan. 1, 2010, pp. 1-18.
Kumbar et al., "Electrospun Nanofiber Scaffolds: Engineering Soft Tissues", Biomaterials, vol. 3, No. 3, Aug. 8, 2008, p. 034002.
Labriola et al., "Fabricating Polyacrylamide Microbeads by Inverse Emulsification to Mimic the Size and Elasticity of Living Cells", Biomaterials Science, vol. 5, No. 1, Dec. 1, 2017, pp. 41-45.
Langer et al., "Polymers for the Sustained Release of Proteins and Other Macromolecules", Nature, vol. 263, No. 5580, Oct. 28, 1976, pp. 797-800.
Lautscham et al., "Biomembrane-Mimicking Lipid Bilayer System as a Mechanically Tunable Cell Substrate", Biomaterials, vol. 35, No. 10, Mar. 2014, pp. 3198-3207.
Lee et al., "Growth Factor Delivery-Based Tissue Engineering: General Approaches and a Review of Recent Developments", Journal of the Royal Society, Interface, vol. 8, No. 55, Feb. 6, 2011, pp. 153-170.
Leong et al., "Inverse Microemulsion Polymerization", J. Phys. Chem., vol. 86, No. 13, 1982, pp. 2269-2271.
Loh et al., "Three-Dimensional Scaffolds for Tissue Engineering Applications: Role of Porosity and Pore Size", Tissue Engineering Part B: Reviews, vol. 19, No. 6, Dec. 2013, pp. 485-502.
Lok et al., "Particle Size Control in Dispersion Polymerization of Polystyrene", Can. J. Chem., vol. 63, 1985, pp. 209-216.
Lopez-Fagundo et al., "A Biomimetic Synthetic Feeder Layer Supports the Proliferation and Self-Renewal of Mouse Embryonic Stem Cells", Acta Biomater., vol. 39, Jul. 15, 2016, pp. 55-64.
Luk et al., "Interfacial Interactions Between Natural RBC Membranes and Synthetic Polymeric Nanoparticles", Nanoscale, vol. 6, No. 5, Mar. 7, 2014, pp. 2730-2737.
Luo et al., "Cancer-Targeted Polymeric Drugs", Curr. Cancer Drug Targets, vol. 2, No. 3, Sep. 2002, pp. 209-226.
Lvov et al., "Alternate Assembly of Ordered Multilayers of SiO2 and Other Nanoparticles and Polyions", Langmuir, vol. 13, 1997, pp. 6195-6203.
Marsich et al., "Alginate/Lactose-Modified Chitosan Hydrogels: A Bioactive Biomaterial for Chondrocyte Encapsulation", Journal of Biomedical Materials Research, vol. 84 A, Issue 2, Dec. 14, 2007, pp. 364-376.
McAllister et al., "Polymeric Nanogels Produced via Inverse Microemulsion Polymerization as Potential Gene and Antisense Delivery Agents", J. Am. Chem. Soc., vol. 124, No. 51, Nov. 28, 2002, pp. 15198-15207.
McBeath et al., "Cell Shape, Cytoskeletal Tension, and RhoA Regulate Stem Cell Lineage Commitment", Developmental Cell, vol. 6, Issue 4, Apr. 2004, pp. 483-495.
Menter, "Acrylamide Polymerization—A Practical Approach", BIO-RAD, Electrophoresis, Tech Note 1156, 2000, 8 pages.
Merkel et al., "Using Mechanobiological Mimicry of Red Blood Cells to Extend Circulation Times of Hydrogel Microparticles", PNAS, vol. 108, No. 2, Jan. 11, 2011, pp. 586-591.
Mishra et al., "PEGylation Significantly Affects Cellular Uptake and Intracellular Trafficking of Non-Viral Gene Delivery Particles", Eur. J. Cell Biol., vol. 83, 2004, pp. 97-111.
Mullier et al., "More On: Calibration for the Measurement of Microparticles: Needs, Interests, and Limitations of Calibrated Polystyrene Beads for Flow Cytometry-Based Quantification of Biological Microparticles", J. Thromb. Haemost., vol. 9, No. 8, Aug. 2011, pp. 1679-1681.
Napolitano et al., "Scaffold-Free Three-Dimensional Cell Culture Utilizing Micromolded Nonadhesive Hydrogels", Biotechniques., vol. 43, No. 4, Oct. 2007, pp. 496-500.
Nii et al., "Encapsulation Efficiency of Water-Soluble and Insoluble Drugs in Liposomes Prepared by the Microencapsulation Vesicle Method", International Journal of Pharmaceutics, vol. 298, Issue 1, Jul. 14, 2005, pp. 198-205.
Olson et al., "Preparation of Liposomes of Defined Size Distribution by Extrusion Through Polycarbonate Membranes", Biochimica et Biophysica Acta (BBA)—Biomembranes, vol. 557, Issue 1, Oct. 19, 1979, pp. 9-23.
Panyam et al., "Biodegradable Nanoparticles for Drug and Gene Delivery to Cells and Tissue", Advanced Drug Delivery Reviews, vol. 55, Issue 3, Feb. 24, 2003, pp. 329-347.
Parekh et al., "Modulus-Driven Differentiation of Marrow Stromal Cells in 3D Scaffolds That Is Independent of Myosin-Based Cytoskeletal Tension", Biomaterials, vol. 32, No. 9, Mar. 2011, pp. 2256-2264.
Park et al., "Cell-in-Shell Hybrids: Chemical Nanoencapsulation of Individual Cells", Acc. Chem. Res., vol. 49, No. 5, Apr. 29, 2016, pp. 792-800.
Park et al., "Injectable Biodegradable Hydrogel Composites for Rabbit Marrow Mesenchymal Stem Cell and Growth Factor Delivery for Cartilage Tissue Engineering", Biomaterials, vol. 28, No. 21, Jul. 2007, pp. 3217-3227.
Parodi et al., "Biomimetic Functionalization with Leukocyte Membranes Imparts Cell Like Functions to Synthetic Particles", Nat. Nanotechnol, vol. 8, No. 1, Jan. 2013, pp. 61-68.
Peter et al., "Effects of Transforming Growth Factor β1 Released From Biodegradable Polymer Microparticles on Marrow Stromal Osteoblasts Cultured on Poly(Propylene Fumarate) Substrates", Journal of Biomedical Materials Research, vol. 50, No. 3, Mar. 23, 2000, pp. 452-462.
Platen et al., "Poly(2-oxazoline)-Based Microgel Particles for Neuronal Cell Culture", Biomacromolecules, vol. 16, No. 5, Mar. 25, 2015, pp. 1516-1524.
Puig et al., "Microstructured Polyacrylamide Hydrogels Prepared via Inverse Microemulsion Polymerization", Journal of Colloid and Interface Science, vol. 235, Issue 2, Mar. 15, 2001, pp. 278-282.
Reis et al., "Nanoencapsulation I. Methods for Preparation of Drug-Loaded Polymeric Nanoparticles", Nanomedicine: Nanotechnology, Biology and Medicine, vol. 2, Issue 1, Mar. 2006, pp. 8-21.
Riaz, "Liposome Preparation Method", Pakistan Journal of Pharmaceutical Sciences, vol. 9, No. 1, Feb. 1996, pp. 65-77.
Roh et al., "Biphasic Janus Particles With Nanoscale Anisotropy", Nat Mater., vol. 4, No. 10, Sep. 25, 2005, pp. 759-763.
Rolland et al., "Direct Fabrication and Harvesting of Monodisperse, Shape-Specific Nanobiomaterials", J. Am. Chem. Soc, vol. 127, No. 28, Jun. 21, 2005, pp. 10096-10100.

(56) References Cited

OTHER PUBLICATIONS

Rosca et al., "Microparticle Formation and Its Mechanism in Single and Double Emulsion Solvent Evaporation", Journal of Controlled Release, vol. 99, Issue 2, Sep. 30, 2004, pp. 271-280.

Rosen et al., "Adipocyte Differentiation from the Inside Out", Nature Reviews Molecular Cell Biology, vol. 7, No. 12, 2006, pp. 885-896.

Schneider et al., "Functional Core/shell Nanoparticles via Layer-by-layer Assembly. Investigation of the Experimental Parameters for Controlling Particle Aggregation and for Enhancing Dispersion Stability", Langmuir, vol. 24, No. 5, 2008, pp. 1778-1789.

Achilli et al., "Advances in the Formation, Use and Understanding of Multi-Cellular Spheroids", Expert Opin. Biol. Ther., vol. 12, No. 10, Oct. 2012, pp. 1347-1360.

Allemann et al., "In Vitro Extended-Release Properties of Drug-Loaded Poly(DL-lactic Acid) Nanoparticles Produced by a Salting-Out Procedure", Pharm. Res., vol. 10, No. 12, Dec. 1993, pp. 1732-1737.

Anseth et al., "Mechanical Properties of Hydrogels and Their Experimental Determination", Biomaterials, vol. 17, Issue 17, 1996, pp. 1647-1657.

Baraniak et al., "Scaffold-Free Culture of Mesenchymal Stem Cell Spheroids in Suspension Preserves Multilineage Potential", Cell and Tissue Research, vol. 347, No. 3, Aug. 11, 2011, pp. 701-711.

Barichello et al., "Encapsulation of Hydrophilic and Lipophilic Drugs in PLGA Nanoparticles by the Nanoprecipitation Method", Drug Development and Industrial Pharmacy, vol. 25, Issue 4, Mar. 25, 1999, pp. 471-476.

Basmanav et al., "Sequential Growth Factor Delivery From Complexed Microspheres for Bone Tissue Engineering", Biomaterials, vol. 29, Issue 31, Nov. 2008, pp. 4195-4204.

Battino et al., "The Solubility of Gases in Liquids", Chem. Rev., vol. 66, No. 4, Aug. 1, 1966, pp. 395-463.

Bernlohr et al., "Intracellular Lipid-Binding Proteins and Their Genes", Annual Review of Nutrition, vol. 17, Jul. 1997, pp. 277-303.

Bratt-Leal et al., "Incorporation of Biomaterials in Multicellular Aggregates Modulates Pluripotent Stem Cell Differentiation", Biomaterials., vol. 32, No. 1, Jan. 2011, pp. 48-56.

Bruder et al., "Fabrication of Polymeric Replicas of Cell Surfaces with Nanoscale Resolution", Langmuir, vol. 22, No. 20, 2006, pp. 8266-8270.

Capek, "The Inverse Mini-Emulsion Polymerization of Acrylamide", Designed Monomers and Polymers, vol. 6, Issue 4, Apr. 2, 2012, pp. 399-409.

Caruso et al., "Enzyme Encapsulation in Layer-by-Layer Engineered Polymer Multilayer Capsules", Langmuir, vol. 16, No. 4, Jan. 29, 2000, pp. 1485-1488.

Cesarz et al., "Spheroid Culture of Mesenchymal Stem Cells", Stem Cells International, vol. 2016, Article ID 9176357, 2016, pp. 1-11.

Champion et al., "Role of Target Geometry in Phagocytosis", PNAS, vol. 103, No. 13, Mar. 28, 2006, pp. 4930-4934.

Champion et al., "Shape Induced Inhibition of Phagocytosis of Polymer Particles", Pharm. Res., vol. 26, No. 1, Jan. 2009, pp. 244-249.

Chan et al., "A Microplate Compression Method for Elastic Modulus Measurement of Soft and Viscoelastic Collagen Microspheres", Annals of Biomedical Engineering, vol. 36, Issue 7, Jul. 2008, pp. 1254-1267.

Chandler et al., "A New Microparticle Size Calibration Standard for Use Inmeasuring Smaller Microparticles Using a New Flow Cytometer", Journal of Thrombosis and Haemostasis, vol. 9, Jun. 2011, pp. 1216-1224.

Cheng et al., "Short-Term Spheroid Formation Enhances the Regenerative Capacity of Adipose-Derived Stem Cells by Promoting Stemness, Angiogenesis, and Chemotaxis", Stem Cells Translational Medicine, vol. 2, No. 8, Jul. 11, 2013, pp. 584-594.

Chrambach et al., "Polyacrylamide Gel Electrophoresis", Science, vol. 172, Issue 3982, Apr. 30, 1971, pp. 440-451.

Christopher et al., "Microfluidic Methods for Generating Continuous Droplet Streams", J. Phys. D, Appl., Phys., vol. 40, Sep. 21, 2007, pp. R319-R336.

Dado et al., "Cell-Scaffold Mechanical Interplay Within Engineered Tissue", Seminars in Cell & Developmental Biology, vol. 20, Issue 6, Aug. 2009, pp. 656-664.

Darling et al., "High-Throughput Assessment of Cellular Mechanical Properties", Annual Review of Biomedical Engineering, vol. 17, Dec. 2015, pp. 35-62.

Darling et al., "Viscoelastic Properties of Human Mesenchymally-Derived Stem Cells and Primary Osteoblasts, Chondrocytes, and Adipocytes", J. Biomech., vol. 41, No. 2, 2008, pp. 454-464.

Darling et al., "Viscoelastic Properties of Zonal Articular Chondrocytes Measured by Atomic Force Microscopy", Osteoarthritis and Cartilage, vol. 14, Issue 6, Jun. 2006, pp. 571-579.

Decuzzi et al., "Size and Shape Effects in the Biodistribution of Intravascularly Injected Particles", Journal of Controlled Release, vol. 141, Issue 3, Feb. 5, 2010, pp. 320-327.

Desai et al., "Gastrointestinal Uptake of Biodegradable Microparticles: Effect of Particle Size", Pharmaceutical Research, vol. 13, No. 12, Dec. 1996, pp. 1838-1845.

Dimitriadis et al., "Determination of Elastic Moduli of Thin Layers of Soft Material Using the Atomic Force Microscope", Biophysical Journal, vol. 82, No. 5, May 2002, pp. 2798-2810.

Doshi et al., "Red Blood Cell-Mimicking Synthetic Biomaterial Particles", PNAS, vol. 106, No. 51, Dec. 22, 2009, pp. 21495-21499.

Dutta et al., "Cell-Interactive 3D-Scaffold; Advances and Applications", Biotechnology Advances, vol. 27, Issue 4, Jul.-Aug. 2009, pp. 334-339.

Dutta et al., "Comprehension of ECM—Cell Dynamics: A Prerequisite for Tissue Regeneration", Biotechnology Advances, vol. 28, No. 6, Nov. 2010, pp. 764-769.

Engler et al., "Matrix Elasticity Directs Stem Cell Lineage Specification", Cell, vol. 126, Issue 4, Aug. 25, 2006, pp. 677-689.

Estes et al., "Monolayer Cell Expansion Conditions Affect the Chondrogenic Potential of Adipose-Derived Stem Cells", Biotechnology and Bioengineering, vol. 99, No. 4, Mar. 1, 2008, pp. 986-995.

Fang et al., "Cancer Cell Membrane-Coated Nanoparticles for Anticancer Vaccination and Drug Delivery", Nano Letters, vol. 14, 2014, pp. 2181-2188.

Gao et al., "Stem Cell Shape Regulates a Chondrogenic Versus Myogenic Fate Through Rac1 and N-Cadherin", Stem Cells, vol. 28, No. 3, Mar. 31, 2010, pp. 564-572.

Ghorbaniazar et al., "Preparation of Poly Acrylic Acid-Poly Acrylamide Composite Nanogels by Radiation Technique", Adv. Pharm. Bull., vol. 5, No. 2, Jun. 2015, pp. 269-275.

Gonzalez-Cruz et al., "Cellular Mechanical Properties Reflect the Differentiation Potential of Adipose-Derived Mesenchymal Stem Cells", PNAS, vol. 109, No. 24, Jun. 12, 2012, pp. E1523-E1529.

Gossett et al., "Hydrodynamic Stretching of Single Cells for Large Population Mechanical Phenotyping", PNAS, vol. 109, No. 20, May 15, 2012, pp. 7630-7635.

Gossett et al., "Label-Free Cell Separation and Sorting in Microfluidic Systems", Analytical and Bioanalytical Chemistry, vol. 397, Issue 8, Aug. 2010, pp. 3249-3267.

Gratton et al., "Nanofabricated Particles for Engineered Drug Therapies: A Preliminary Biodistribution Study of Print™ Nanoparticles", Journal of Controlled Release, vol. 121, Issues 1-2, Aug. 16, 2007, pp. 10-18.

Han et al., "Cartilage Regeneration Using Adipose-Derived Stem Cells and the Controlled-Released Hybrid Microspheres", Joint Bone Spine, vol. 77, Issue 1, Jan. 2010, pp. 27-31.

Harris et al., "Pegylation: A Novel Process for Modifying Pharmacokinetics", Clin. Pharmacokinet, vol. 40, No. 7, 2001, pp. 539-551.

Hasirci et al., "High Strength Bioresorbable Bone Plates: Preparation, Mechanical Properties and in Vitro Analysis", Bio-Medical Materials Engineering, vol. 10, No. 1, Feb. 23, 2000, pp. 19-29.

Hayashi et al., "Preparation of Stem Cell Aggregates with Gelatin Microspheres to Enhance Biological Functions", Acta Biomaterialia, vol. 7, Issue 7, Jul. 2011, pp. 2797-2803.

(56) References Cited

OTHER PUBLICATIONS

Herzenberg et al., "The History and Future of the Fluorescence Activated Cell Sorter and Flow Cytometry: A View from Stanford", Clinical Chemistry, vol. 48, No. 10, 2002, pp. 1819-1827.
Hielscher et al., "Influence of Particle Size and Concentration on the Diffuse Backscattering of Polarized Light From Tissue Phantoms and Biological Cell Suspensions", Applied Optics, vol. 36, Issue 1, 1997, pp. 125-135.
Ho et al., "Preparation of Monodisperse Ellipsoidal Polystyrene Particles", Colloid and Polymer Science, vol. 271, Issue 5, May 1993, pp. 469-479.
Hollister, "Porous Scaffold Design for Tissue Engineering", Nature Materials, vol. 4, Jul. 1, 2005, pp. 518-524.
Hu et al., "Erythrocyte Membrane-Camouflaged Polymeric Nanoparticles as a Biomimetic Delivery Platform", PNAS, vol. 108, No. 27, Jul. 5, 2011, pp. 10980-10985.
Hu et al., "Nanoparticle Biointerfacing by Platelet Membrane Cloaking", Nature, vol. 526, No. 7571, Oct. 1, 2015, pp. 118-121.
Huang et al., "On the Importance and Mechanisms of Burst Release in Matrix-Controlled Drug Delivery Systems", Journal of Controlled Release, vol. 73, 2001, pp. 121-136.
Singh et al., "Microsphere-Based Scaffolds for Cartilage Tissue Engineering: Using Sub-Critical CO2 as a Sintering Agent§", Acta Biomater., vol. 6, No. 1, Jan. 2010, pp. 137-143.
Sokolsky-Papkov et al., "Polymer Carriers for Drug Delivery in Tissue Engineering", Advanced Drug Delivery Reviews, vol. 59, Issues 4-5, May 30, 2007, pp. 187-206.
Solon et al., "Fibroblast Adaptation and Stiffness Matching to Soft Elastic Substrates", Biophysical Journal, vol. 93, Dec. 2007, pp. 4453-4461.
Stadler et al., "A Critical Look at Multilayered Polymer Capsules in Biomedicine: Drug Carriers, Artificial Organelles, and Cell Mimics", Advanced Functional Materials, vol. 21, No. 1, Jan. 7, 2011, pp. 14-28.
Sudimack et al., "Targeted Drug Delivery via the Folate Receptor", Advanced Drug Delivery Reviews, vol. 41, Issue 2, Mar. 30, 2000, pp. 147-162.
Suh et al., "An Angiogenic, Endothelial-Cell-Targeted Polymeric Gene Carrier", Molecular Therapy, vol. 6, No. 5, Nov. 2002, pp. 664-672.
Szoka et al., "Comparative Properties and Methods of Preparation of Lipid Vesicles (Liposomes)", Annu. Rev. Biophys. Bioeng., vol. 9, 1980, pp. 467-508.
Tang et al., "The Regulation of Stem Cell Differentiation by Cell-Cell Contact on Micropatterned Material Surfaces", Biomaterials, vol. 31, Issue 9, Mar. 2010, pp. 2470-2476.
Tang et al., "Therapeutic Microparticles Functionalized with Biomimetic Cardiac Stem Cell Membranes and Secretome", Nature Communications, vol. 8, No. 13724, Jan. 3, 2017, pp. 1-9.
Toledano Furman et al., "Reconstructed Stem Cell Nanoghosts: A Natural Tumor Targeting Platform", Nano Lett., vol. 13, No. 7, Jun. 20, 2013, pp. 3248-3255.
Tse et al., "Preparation of Hydrogel Substrates With Tunable Mechanical Properties", Current Protocols in Cell Biology, vol. 47, Issue 1, Jun. 2010, pp. 10.16.1-10.16.16.
Tseng et al., "Uniform Polymer Particles by Dispersion Polymerization in Alcohol", Polymer Chemistry Edition, vol. 24, 1986, pp. 2995-3007.
Van Vlerken et al., "Multi-Functional Polymeric Nanoparticles for Tumour-Targeted Drug Delivery", Expert Opin. Drug Deliv., vol. 3, No. 2, Mar. 2006, pp. 205-216.
Villa et al., "Red Blood Cells: Supercarriers for Drugs, Biologicals, and Nanoparticles and Inspiration for Advanced Delivery Systems", Adv Drug Deliv Rev., vol. 106, Nov. 15, 2016, pp. 88-103.
Wang et al., "Co-Delivery of Drugs and DNA from Cationic Core-Shell Nanoparticles Self-Assembled from a Biodegradable Copolymer", Nature Materials, vol. 5, No. 10, Sep. 24, 2006, pp. 791-796.
Wang et al., "Synthesis and Evaluation of Water-Soluble Polymeric Bone-Targeted Drug Delivery Systems", Bioconjugate Chem., vol. 14, No. 5, Aug. 20, 2003, pp. 853-859.
Whelan et al., "Collagen I Initiates Endothelial Cell Morphogenesis by Inducing Actin Polymerization through Suppression of Cyclic AMP and Protein Kinase A", The Journal of Biological Chemistry, vol. 278, No. 1, Jan. 3, 2003, pp. 327-334.
Xu et al., "Cell Stiffness Is a Biomarker of the Metastatic Potential of Ovarian Cancer Cells", Plos One, vol. 7, Issue 10, e46609, Oct. 2012, pp. 1-12.
Xu et al., "Generation of Monodisperse Particles by Using Microfluidics: Control Over Size, Shape, and Composition", Angewandte Chemie, vol. 44, Issue 5, Jan. 21, 2005, pp. 724-728.
Xu et al., "Preparation of Monodisperse Biodegradable Polymer Microparticles Using a Microfluidic Flow-Focusing Device for Controlled Drug Delivery", Small, vol. 5, No. 13, Jul. 3, 2009, pp. 1575-1581.
Yamada et al., "Cell-Sized Condensed Collagen Microparticles for Preparing Microengineered Composite Spheroids of Primary Hepatocytes", Lab on a Chip, vol. 15, 2015, pp. 3941-3951.
Yan et al., "Assembly of Layer-by-Layer Particles and Their Interactions with Biological Systems", Chem. Mater., vol. 26, No. 1, Aug. 22, 2013, pp. 452-460.
Yeung et al., "Effects of Substrate Stiffness on Cell Morphology, Cytoskeletal Structure, and Adhesion", Cell Motil Cytoskeleton., vol. 60, No. 1, Jan. 2005, pp. 24-34.
Zhang et al., "Controllable Microfluidic Strategies for Fabricating Microparticles Using Emulsions as Templates", Particuology, vol. 24, Feb. 2016, pp. 18-31.
Zhu et al., "Stimuli-Responsive Controlled Drug Release from a Hollow Mesoporous Silica Sphere/Polyelectrolyte Multilayer Core-Shell Structure", Angew. Chem. Int. Ed. Engl., vol. 44, No. 32, Aug. 12, 2005, pp. 5083-5087.
Estes BT, Diekman BO, Gimble JM, Guilak F. Isolation of adipose-derived stem cells and their induction to a chondrogenic phenotype. Nat Protoc. 2010;5(7):1294-1311. doi:10.1038/nprot.2010.81.
Janes KA, Albeck JG, Gaudet S, Sorger PK, Lauffenburger DA, Yaffe MB. A systems model of signaling identifies a molecular basis set for cytokine-induced apoptosis. Science. Dec. 9, 2005;310(5754):1646-53. doi: 10.1126/science.1116598. PMID: 16339439.
Ikuyo Nakajima, Hisashi Aso, Takahiro Yamaguchi, Kyouhei Ozutsumi, "Adipose tissue extracellular matrix: newly organized by adipocytes during differentiation," Differentiation, vol. 63, Issue 4, 1998, pp. 193-200, ISSN 0301-4681, https://doi.org/10.1111/j.1432-0436.1998.00193.x.
Nobusue, H., Onishi, N., Shimizu, T. et al. Regulation of MKL1 via actin cytoskeleton dynamics drives adipocyte differentiation. Nat Commun 5, 3368 (2014). https://doi.org/10.1038/ncomms 4368.
Sart S, Tsai AC, Li Y, Ma T. Three-dimensional aggregates of mesenchymal stem cells: cellular mechanisms, biological properties, and applications. Tissue Eng Part B Rev. Oct. 2014;20(5):365-80. doi: 10.1089/ten.TEB.2013.0537. Epub Dec. 13, 2013. PMID: 24168395; PMCID: PMC4185975.
Silver, Nicholas & Best, Steve & Jiang, Jie & Thein, Swee. (2006). Silver N, Best S, Jiang J, Thein SL. Selection of housekeeping genes for gene expression studies in human reticulocytes using real-time PCR. BMC Molecular Biology. BMC molecular biology. 7. 33. 10.1186/1471-2199-7-33.
Tanaka S, Wands JR. Insulin receptor substrate 1 overexpression in human hepatocellular carcinoma cells prevents transforming growth factor beta1-induced apoptosis. Cancer Res. Aug. 1, 1996;56(15):3391-4. PMID: 8758899.
Zheng B, Cao B, Li G, Huard J. Mouse adipose-derived stem cells undergo multilineage differentiation in vitro but primarily osteogenic and chondrogenic differentiation in vivo. Tissue Eng. Jul. 2006;12(7):1891-901. doi: 10.1089/ten.2006.12.1891. PMID: 16889519.

\* cited by examiner

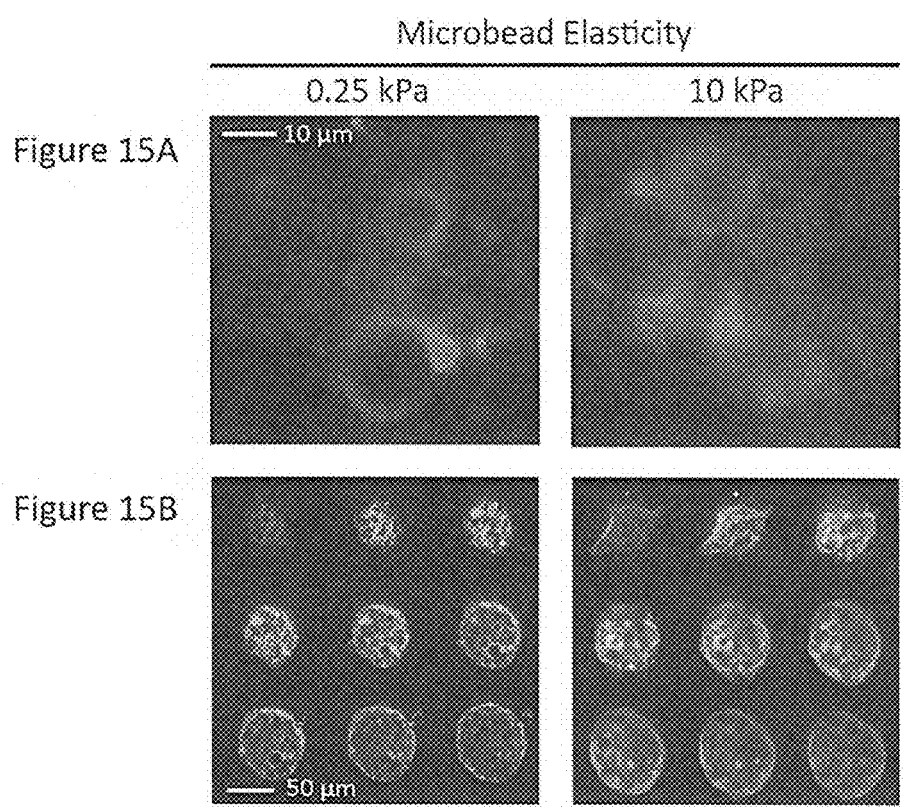

METHODS OF FABRICATING HYPER COMPLIANT POLYMER PARTICLES AND METHODS OF USE AND COMPOSITIONS

CROSS REFERENCE TO RELATED APPLICATIONS

The present application is a national phase filing under 35 U.S.C. § 371 of International Application No. PCT/US2017/063825 filed Nov. 30, 2017, which claims benefit of provisional application No. 62/428,029 filed Nov. 30, 2016 entitled, "Methods of fabricating hyper compliant polymer particles and methods of use and compositions", with inventors Eric M. Darling, Nicholas R. Labriola, and Edith Mathiowitz and provisional application No. 62/520,066 filed Jun. 15, 2017 entitled, "Methods of fabricating hyper compliant polymer particles and methods of use and compositions", with inventors Eric M. Darling, Nicholas R. Labriola, and Edith Mathiowitz, each of which is hereby incorporated by reference herein in its entirety.

GOVERNMENT SUPPORT

This invention was made with government support under grants P20 GM 104937 and R01 AR063642 awarded by the National Institutes of Health and CBET1253189 awarded by the National Science Foundation. The government has certain rights in the invention.

TECHNICAL FIELD

The present invention relates to methods of fabrication of polymer particles and uses of polymer particles in calibration, in medical devices, and other industrial uses.

BACKGROUND

Polymer microparticles have been used extensively in biomedical sciences for example: drug delivery, tissue engineering, and encapsulation among others. Such particles have been produced through a variety of methodologies, including microfluidics (Xu, S. et al. *Angew Chem*, 2005, 117, 734-738; Christopher, G. F. et al. *J. Phys. D: Appl. Phys.*, 2007, 40, 319-336) layer-by-layer deposition (Lvov, Y. et al. *Langmuir*, 1997, 13, 6195-6203) particle replication in non-wetting templates (Rolland, J. P. et al. *J. Am. Chem. Soc.*, 2005, 127, 10096-10100) hydroelectrodynamic jetting (Doshi, N. et al. *Nature Materials*, 2005, 4, 759-763), dispersion polymerization (Lok, K. P. et al. *Can. J. Chem.*, 1985, 63, 209-216; Tseng, C. M. et al. *J. Polymer Sci. Pt. A*, 1986, 24, 2995-3007), and emulsification (Leong, Y. S. et al. *J Phys. Chem.*, 1982, 86(13), 2269-2271; McAllister, K. et al. *J. Am. Chem. Soc.*, 2002, 124, 15198-15207), among others. The differences associated with these methodologies result in varying levels of compatibility with specific polymers, as well as different particle elasticity and size distributions (FIG. 1).

Importantly, there is currently a gap in availability of cell mimicking microparticles (CMMP) of ranges of the sizes (Lo Surdo, J. et al. *Applied Optics*, 1997, 36(1), 125-135) and elasticities (0.1-5 kPa; Darling, E. M. et al. *J. Biomech*, 2008, 41, 454-464; Gonzalez-Cruz, R. D. et al. *PNAS*, 2012, 109, E1523-1529; Kanthilal, M. et al. *Cel. Mol. Bioeng.*, 2014, 7(4), 585-597; Darling, E. M. et al. *Annj. Rev. Biomed Eng.* 2015, 17, 35-62) that are similar to living cells. There is a need for fabrication of microparticles/microbeads with characteristics that mimic cell elasticity, size, and spherical shape.

SUMMARY

An aspect of the invention herein provides a method of making hyper compliant polymer particles by inverse emulsification, the method including:
preparing a monomer solution in a degassed dispersed mixture of an organic surfactant in an organic solvent to obtain a polymerization mixture; and
cross-linking the polymerization mixture with an initiating agent by stirring under vacuum to obtain by inverse emulsification the hyper compliant polymer particles.

The phrase "hyper compliant polymer particles" shall mean herein and in the claims, particles made of natural or synthetic materials that are highly deformable and that have a Young's modulus threshold or mechanical compliance from at least about 0.01 kPascals (kPa; note that 0.01 kPa is 10 Pascals or 10 Pa) to at least about 10 kPa or at least about 15 kPa. These parameters are understood to have a statistical variance of plus or minus 5% to 10%. These particles are thus softer than those previously described.

An embodiment of the method further optionally includes straining the hyper compliant polymer particles through at least one micro filter having pores less than about 100 micrometers (µm), to obtain a monodispersed uniform sized population of hyper compliant polymer particles of a predetermined size. Alternatively, microfluidic devices with inertial focusing or Dean's flow can sort a heterogeneous population of hyper compliant polymer particles into monodispersed uniform sized subpopulations. In an alternative embodiment, FACS sorters are used to sort heterogeneous sized hyper compliant polymer particle populations into monodispersed uniform sized subpopulations by measurements of forward scatter (FSC).

The term "straining" refers to filtration to remove unwanted particles of larger size than desired size ranges. The hyper compliant polymer particles are filtered through a micro filter such that the large, unwanted particles are removed and small, preferred particles pass through into the filtrate. The word, "monodisperse" as referring to hyper compliant polymer particles shall mean herein and in the claims that the particles are characterized by uniform size, shape or mass in a dispersed phase, forming a single peak chromatographically.

Another embodiment of the method further includes coating the hyper compliant polymer particles with at least one material selected from: a protein, a nucleotide sequence, a carbohydrate, a lipid, a cell plasma membrane, and a small molecule. An embodiment of the method further includes coating the hyper compliant polymer particles with at least one material selected from: a therapeutic agent, and a targeting agent.

In an embodiment of the method the protein is at least one selected from: a collagen, a cadherin, a fibrin, an actin, a thrombin, a laminin, and an albumin. In an embodiment of the method, the mechanical compliance (Young's modulus) of the hyper compliant polymer particles is less than about 10 kPa. In an embodiment of the method, the monomer is water-soluble and cross-linked polymer is water-swellable. The phrase "water-swellable" shall mean herein and in the claims, a water-absorbing polymer, which is classified as a hydrogel when cross-linked and which absorbs aqueous solutions through hydrogen bonding with water molecules. The polymer is polymerized from a monomer, which is optionally water-soluble. In an embodiment of the method, the polymer is at least one selected from: polyacrylamide, poly(N-vinyl formamide), polyethylene oxide, polyethylene glycol, agarose, alginate, a collagen, a chitin, a fibrin, chondroitin sulfate, and hyaluronic acid. Other examples of suitable polymers include polydimethyl siloxane (PDMS), dendrimers, star polymers, and bioerodible polymers. In an embodiment of the method, the initiating agent is a tertiary amine, or a riboflavin. In various embodiments the hyper compliant polymer particles have a diameter less than about 100 µm.

An aspect of the invention herein provides a hyper compliant polymer particle composition which contains hyper compliant polymer particles having a predetermined mechanical compliance and a predetermined size with a monodisperse diameter within a range of about 0.1 µm to about 100 µm, or within a range of about 1 µm to about 50 µm, or within a range of about 5 µm to about 40 µm.

In an embodiment of the composition an agent is encapsulated within the particles. For example, the agent is at least one selected from: a radioactive probe, a therapeutic agent, a fluorescent dye, a colorimetric dye, a protein, a nucleotide sequence, a carbohydrate, a lipid, an antibody, a small molecule, and a magnet or a magnetically resonant particle. In various embodiments of the composition, the predetermined mechanical compliance is less than about 10 kPa.

An embodiment of the composition further includes a coating of the hyper compliant polymer particles with at least one material selected from: a protein, a nucleotide sequence, a carbohydrate, a lipid, a microparticle, a nanoparticle, and a small molecule. For example, a coating of the hyper compliant polymer particles is at least one material selected from: a therapeutic agent, and a targeting agent. In an embodiment of the composition, the hyper compliant polymer particles are obtained by inverse emulsification. In an embodiment of the composition, the agent encapsulated within the particles is a microparticle containing a therapeutic agent or a nanoparticle containing a therapeutic agent. In an embodiment of the composition, viscoelasticity of the microparticle or the nanoparticle is distinct from viscoelasticity of the hyper compliant polymer particles. In an embodiment of the composition, the therapeutic agent in the microparticle or the nanoparticle is released at a predetermined rate. For example, a microparticle containing a therapeutic agent is encapsulated in a hyper compliant polymer particle. The properties of the microparticle are such that the therapeutic agent in the microparticle has an extended release or is released slowly over time. Alternatively, the therapeutic agent in the microparticle is eluted fast or in a burst.

An aspect of the invention provides a use of the composition described herein for at least one of: drug delivery, assay, particle image velocimetry, ceramics, cosmetics, deconvolution, electronic paper, insulation, personal care, standards, retroreflective paint and paint applications, thickening agents, regenerative medicine, device calibration, micro-carriers, and force indicators.

An aspect of the invention herein provides a method of calibrating a flow device for particle sizes in the range of cell sizes, the method including:
preparing a fluid containing a hyper compliant polymer particle composition obtained by inverse emulsification and having a predetermined mechanical compliance and a predetermined diameter selected by the user within a range of about 0.1 µm to about 100 µm; and
impelling the fluid through the flow device and measuring voltage as the hyper compliant polymer particles deform while flowing through the flow device thereby calibrating the flow device to a value accurate for cells, for example the cells are mammalian cells and the predetermined diameter of the particles is about 15 µm or the cells are bacterial cells and the predetermined diameter of the cells is about 1-3 µm.

In an embodiment of the method, the flow device is at least one selected from: a flow cytometer, a fluorescence-activated cell sorting (FACS) device, and a micro-fluidic device. An embodiment of the method further includes coating the hyper compliant polymer particles at least one material selected from: a therapeutic agent, a protein, a nucleotide sequence, a targeting agent, a carbohydrate, a lipid, a dye, and a small molecule. Particles in another embodiment may be coated metal particles, for example the particle is coated with a metal which is a precious metal such as gold or silver, or the metal is magnetic or paramagnetic, such as an iron oxide, or the particles may encapsulate the metal or a ceramic.

An aspect of the invention herein provides a method of drug delivery with a hyper compliant polymer particle, the method including:
linking a therapeutic agent to or encapsulating the therapeutic agent within the hyper compliant polymer particle obtained by inverse emulsification and having a predetermined mechanical compliance and a predetermined diameter of monodisperse size within a range of about 0.1 µm to about 100 µm, to obtain a resulting therapeutic hyper compliant polymer particle composition; and
administering the composition to a subject.

An embodiment of the method further includes prior to administering, coating the therapeutic hyper compliant polymer particle with a targeting agent such as an antibody or a binding protein or alternatively the mechanical properties of the therapeutic hyper compliant polymer particle may serve as a targeting mechanism.

An aspect of the invention herein provides a method of making hyper compliant polyacrylamide particles by inverse emulsification, the method including:
preparing a monomer solution having acrylamide, bis-acrylamide, ammonium persulfate and initiating polymerization with a N,N,N',N'-tetramethylethylenediamine (TEMED) polymerization initiator in an aqueous solution to obtain a polymer solution;
adding the polymer solution to a degassed dispersed mixture of cyclohexane and polysorbate 85 to obtain to obtain an emulsification mixture; and
stirring the emulsification mixture under vacuum to obtain the hyper compliant polyacrylamide particles.

The TEMED used in the method is generally in an aqueous solution, which is a buffer such as phosphate-buffered saline.

An embodiment of the method further includes filtering the hyper compliant polyacrylamide particles through a micro-filter to obtain a monodisperse particle population having particles of uniform diameter. An alternative embodiment of the method further includes filtering the hyper compliant polyacrylamide particles sequentially through a plurality of micro-filters, each micro-filter having respectively smaller pore sizes than preceding micro-filters, to obtain a monodisperse particle population having particles of uniform diameter. An embodiment of the method further includes cross-linking or covalently-linking the hyper compliant polyacrylamide particles with at least one selected from: a collagen, a protein, a nucleotide sequence, a carbohydrate, a lipid, an antibody, and a small molecule to obtain cell adhesive hyper compliant polyacrylamide particles. In an embodiment of the method, the diameter is selected from about 5 µm, about 10 µm, about 15 µm, about 20 µm, about 25 µm, about 30 µm, about 35 µm, and about 40 µm.

An aspect of the invention herein provides a method for generating or regenerating a target mammalian tissue or organ, the method including:
  contacting cells from the target mammalian tissue with hyper compliant polymer particles obtained by inverse emulsification and having a predetermined mechanical compliance and a diameter of about 0.1 µm to about 100 µm, the diameter selected to conform to that of the tissue or organ; and
  adding cell growth medium to the cells and the hyper compliant polymer particle composition and analyzing stimulation of the generation or regeneration of newly grown cells of the target tissue or organ.

An aspect of the invention herein provides a method for calculating applied force in a device or a fluid flow, the method including:
  preparing a fluid containing hyper compliant polymer particles obtained by inverse emulsification and having a predetermined mechanical compliance and a diameter of about 0.1 µm to about 100 µm;
  impelling the fluid in the device or the fluid flow; and
  measuring an extent of deformation of the hyper compliant polymer particle; such that the extent of deformation of the hyper compliant polymer particles is directly proportional to applied force and calculating applied force in the device or the fluid flow.

An embodiment of the invention provides in a method of calibrating a flow device using a standard of beads such as polystyrene beads having a greater rigidity than a biological sample containing mammalian cells, the improvement includes calibrating the device using hyper complaint polymer particles prepared according to the method described herein.

An aspect of the invention herein provides a device including differentiated adipose tissue, dividing aggregated stem cells, and biodegradable hyper compliant polymer particles, in a sterile medium and in an amount and form suitable for transplantation into a subject in need of the tissue, the differentiated tissue arising from the stem cells.

In an embodiment of the device, the stem cells and the subject are autologous; in an alternative embodiment, the stem cells and the subject are heterologous. The word, "autologous" means that donor cells are from the same subject as the recipient. The word, "heterologous" means that the donor cells are from a source other than the subject recipient.

An aspect of the invention herein provides a method of treating a subject in need of an adipose transplant including:
  contacting stem cells with biodegradable hyper compliant polymer particles and culturing the cells and particles under aseptic conditions in a sterile growth medium for replication and differentiation into adipose tissue of the stem cells, the stem cells aggregating with the particles; and
  surgically implanting differentiated adipose tissue into the subject.

In an embodiment of the method, the recipient subject in need is treated for at least one condition selected from the group of: trauma for example from gunshot or industrial wound; cachexia; breast reconstruction; and cosmetic surgery.

An aspect of the invention herein provides a method for calculating in situ stress in a tissue, the method including:
  preparing at least one composition including hyper compliant polymer particles having a predetermined mechanical compliance and a diameter;
  incubating each of the hyper compliant polymer particle compositions with cells of the tissue; and
  measuring an extent of deformation of the hyper compliant polymer particles; such that the extent of deformation of the hyper compliant polymer particles is directly proportional to in situ stress in the tissue.

The phrase "in situ stress" shall mean herein and in the claims, the contractile and tensile forces exerted on a particle by surrounding cells in context of a tissue, or in a cell culture, in which context the particle is mimicking cells of the tissue and the extent of stress on the particle is a measure of stress experienced by a cell of the organism.

An embodiment of the method further including prior to incubating, cloaking the hyper compliant polymer particles with at least one material selected from: a therapeutic agent, a protein, a nucleotide sequence, a targeting agent, a carbohydrate, a lipid, a dye, and a small molecule. The words, "cloaking" and "coating" shall mean herein and in the claims, a covering that attaches to the exterior each of the particles and possibly extends to the entirety of the particles, in which case the coating encases the particle. For example, the covering can be a red blood cell membrane, a cancer cell membrane, a leukocyte membrane, a cardiovascular membrane, an epithelial membrane, and a neuronal membrane among others.

An embodiment of the method further including prior to incubating, injecting or implanting, the composition into a target tissue in a subject. In an embodiment of the method the recipient subject is a human. In an alternative embodiment of the method the recipient is any mammal or bird or other animal. In yet another embodiment of the method the cells of the tissue either donor or recipient are in a cell culture or a tissue culture. In an embodiment of the method, the composition or the particles are obtained by inverse emulsification.

An aspect of the invention herein provides a method for testing a filter for pore size, the method including:
  preparing a fluid containing at least one composition including hyper compliant polymer particles having a predetermined mechanical compliance and a predetermined diameter;
  impelling the fluid through the filter to obtain a filtrate; and
  measuring at least one parameter selected from: number of hyper compliant polymer particles that are impelled through the filter into the filtrate; flow rate of the fluid impelled through the filter; flow volume impelled through filter as a function of time; and extent of refraction or scatter or reflection of light in the filtrate; thereby determining and testing the filter for pore size.

In an embodiment of the method, the diameter of the hyper compliant polymer particles is at least about 0.1 µm to about 1 µm; at least about 1 µm to about 10 µm; at least about 10 µm to about 50 µm or at least about 50 µm to about 100 µm In an embodiment of the method, the mechanical compliance of the hyper compliant polymer particles is less than about 10 kPa.

An embodiment of the method further includes prior to impelling, measuring number of hyper compliant polymer particles in the fluid, an extent of refraction of light or light scattering in the fluid In an embodiment of the method, preparing includes a first composition and a second composition that have predetermined mechanical compliance and diameters that are not identical.

In an embodiment of the method, measuring further includes adding to at least the first composition a marker selected from: a dye, an enzyme, a radioactive probe, a florescent molecule, an antigen, and an antibody.

An aspect of the invention herein provides a method for preparing cells for cryopreservation, the method including, providing a cell suspension in need of cryopreservation;
preparing a hyper compliant polymer particles suspension having a predetermined mechanical compliance and a predetermined diameter; and contacting the cell suspension and the particle suspension to obtain a cryopreservation suspension thereby preparing the cells for cryopreservation.

In an embodiment of the method the diameter of the hyper compliant polymer particles is at least about 0.1 µm to about 1 µm; at least about 1 µm to about 10 µm; at least about 10 µm to about 50 µm or at least about 50 µm to about 100 µm. In an embodiment of the method the mechanical compliance of the hyper compliant polymer particles is less than about 10 kPa.

An embodiment of the method further includes measuring diameter of cells in need of cryopreservation. In an embodiment of the method the diameter of the hyper compliant polymer particles is equivalent to diameter of cells in need of cryopreservation. In an embodiment of the method the cell suspension has a low density of cells. For example the cell density is less than about one million cells/ml or is less than about $10^5$ cells/ml.

In an embodiment of the method the cells suspension is obtained from at least one source selected from: a biopsy sample, a cell culture, a primary cell culture, a recombinant cell culture, a blood sample, a plasma sample, a tear sample, a saliva sample, and a cord blood sample.

An embodiment of the method further includes prior to contacting, adding dimethyl sulfoxide (DMSO) to the cell suspension. Another embodiment of the method further includes prior to contacting, adding dimethyl sulfoxide (DMSO) to the hyper compliant polymer particles suspension.

BRIEF DESCRIPTION OF THE DRAWINGS

FIG. 2A is graph showing population density histograms for microbeads generated using; 0.1% bis-acrylamide at 1500 RPM with 40 µm filtering (peak on left, 20±7 µm); 1250 RPM (center peak, 48±20 µm); or 700 RPM (peak on right, 104±24 µm). These histograms demonstrate the inverse relationship between stir speed and particle size. The inclusion of 40 µm filtering was observed to yield a much more monodisperse population within the target size range by removing large beads and aggregates.

FIG. 2B is a set of microphotographs that show each bead population obtained by various stir rates corresponding to the histograms in FIG. 2A above each photo. Each microphotograph also includes a bead size as a white "scale microbeads" used which have 25, 50, and 100 µm diameters (left to right).

FIG. 10A is a set of scatter plots of spheroid elastic moduli ($E_{elastic}$) vs. spheroid diameter. The individual data points in these plots are represented by open circles, and the geometric mean and standard deviations are represented by crosshairs for both adipogenic and control spheroids.

FIG. 10B is a set of brightfield images that correspond to the scatter plots and are displayed in a matrix where descending rows are images observed at later time points and columns are images of formulations of increasing stiffness of incorporated microbeads from left to right.

FIG. 15A and FIG. 15B are a set of microphotographs showing that cell mimicking microparticles (CMMPs) within self-assembled, stem cell spheroids serve as probes of in situ stresses by monitoring shape.

FIG. 15A data of 0.25 kPa CMMPs (left) deform to a greater extent than 10 kPa CMMPs (right) in response to the contractile forces of surrounding cells. An accurate reporting of the in situ stresses can be calculated based on the known mechanical properties of the CMMPs and their deformation from an original, spherical shape.

FIG. 15B shows two montages of confocal images (about 60 μm thickness, 7 μm steps), which demonstrate that both 0.25 kPa (left) and 10 kPa (right) microbeads coated in collagen (red) were observed to have been shuttled to the center of cell spheroids. Cell nuclei and actin cytoskeletal structures were stained with DAPI (blue) and Alexa Fluor 488 Phalloidin (green), respectively.

DETAILED DESCRIPTION

Figure 1:
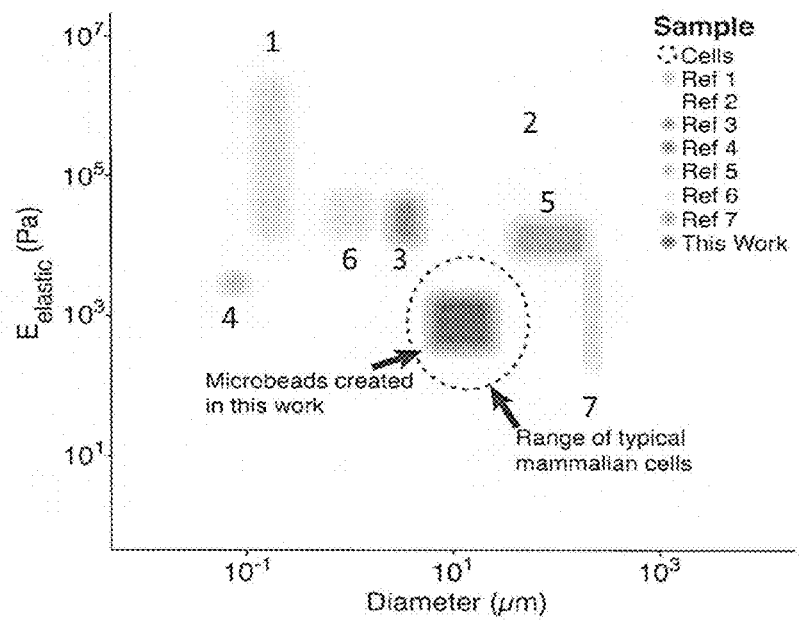
FIG. 1 is a graph comparing particle/bead sizes and elasticity ranges known in the art, to cell sizes. Shaded regions represent the span of microbead diameters and elastic moduli documented in publications (Ref 1: Anselmo, A. C. et al. *ACS Nano*, 2015, 9(3), 3169-3177; Ref 2: Singh, M et al. *Acta Biomaterialia*, 2010, 6(1), 137-143; Merkel, Ref 3: T J et al. *PNAS*, 2011, 108(2), 586-591; Ref 4: Puig, L. J. et al. *J Colloid Interface Sci.*, 2001, 235, 278-282; Ref 5: Platen, M. et al. *Biomacromoledules*, 2015, 16, 1516-1524; Ref 6: Marsich, E. et al. *J. Biomed Mater. Res. A*, 2007, 84(2), 364-376; Ref 7: Chan, B. P. et al. *Annals Biomed. Eng.*, 2008, 36(7), 1254-1267). The dashed circle represents the approximate diameter (about 10 µm) and elastic moduli (about 1 kPa) associated with mammalian cells of spherical morphology (Darling, E. M. et al. *J. Biomech*, 2008, 41, 454-464; Gonzalez-Cruz, R. D. et al. *PNAS*, 2012, 109, E1523-1529; Kanthilal, M. et al. *Cel. Mol. Bioeng.*, 2014, 7(4), 585-597; Darling, E. M. et al. *Annj. Rev. Biomed Eng.* 2015, 17, 35-62). The shaded region inside the dashed circle is the range of microbead diameters and elastic moduli of microparticles provided in the application herein.

Cellular mechanical properties, or mechanophenotype, have increasingly been used as novel biomarkers for identifying specific cell types or disease states. A mechanophenotype can be used for both diagnostic and research purposes, with relevant examples including cancer, sickle cell, and diabetes (Darling, E. M. et al. *Annu. Rev. Biored Eng.*, 2015, 17, 35-62). Microfluidic devices are a means to identify cellular mechanophenotypes and explored, for example, to isolate rare, circulating tumor cells (CTCs) from blood depending on their unique size and deformability (Hur, S. C., et al. *Lab on a Chip*, 2011, 11, 912). However, standardization of this type of equipment can be complicated, especially since reference materials combining size and stiffness do not exist presently. The microbeads provided herein are used to test and calibrate devices or methodologies intended to manipulate, characterize, or sort cells.

Microbeads with high mechanical compliance mimic the stimulatory effect cells receive when adhered to materials with biologically relevant mechanical properties (Engler, A. J. et al. *Cell,* 2006, 126, 677-689). By mechanosensing, cells recognize the stiffness of their substrates and undergo cytoskeletal remodelling that alters cell fate. Because this effect does not require exogenous molecules, there has been increased interest in developing new cell culture systems that use material mechanical properties to direct cell behaviour and physiological responses in general (Gossett, D. R. et al. *Anal Bioanal Chem,* 2010, 397, 3249-3267; Gossett, D R et al. *PNAS,* 2012, 109:(20), 7630-7635). As such, polymer microbeads that mimic the size and mechanical properties of cells have a variety of applications in research involving three-dimensional (3D) culture systems used to study cell responses to physiologically relevant substrate mechanical properties, various surface coatings, and localized delivery of bioactive molecules.

Emulsification is used to produce micro/nano-beads and is compatible with many polymers (Anselmo, A. C. et al. *Adv. Drug Deliv. Rev.,* 2016). The methods described herein uses polyacrylamide (PAAm), a mechanically tunable polymer (Engler, A. J. et al. *Cell,* 2006, 126, 677-689) that relies on free radical initiation (Menter, P. *Bio-Rad Laboratories,* 2000, Tech Note 1156; Capek, I. Designed Monomers and Polymers, 2012, 6(4), 399-409) to form a hydrogel mesh structure, in conjunction with water-in-oil emulsion, or inverse emulsification, to produce "cell-like" microbeads. PAAm offers simple chemistry, rapid polymerization, long-term mechanical and morphological stability, functionalization, and compatibility with protein coatings through NHS ester-mediated cross-linking. PAAm produces reproducible formulations of cross-linked gels with Young's moduli below 1 kPa, which can be problematic for other materials.

The methods provided herein are used to fabricate PAAm microbeads with diameters and mechanical properties similar to cells exhibiting a spherical morphology. The methods described herein create cell-sized (about 5 µm to about 40 µm) PAAm microbeads with tunable mechanical properties (about 0.25 kPa to about 2 kPa) through inverse emulsification. The microbeads were found to be capable of post-polymerization modification such as fluorescent staining and collagen coating.

The methods described herein generate PAAm microbeads that mimic the size and elastic modulus distributions of typical cell populations using a vacuum-maintained inverse emulsification process. The methods described herein control microbead elasticity by altering cross-linker concentration and diameter by varying stir rate in conjunction with filtering. The fully polymerized microbeads are compatible with fluorescent dyes that allow for easy particle visualization. The microbeads described herein can be functionalized with a protein coating to promote cell recognition and binding. The relatively tight distributions of elastic moduli and diameters of microbeads within individual bead populations make them ideal calibration particles for microfluidic devices designed to examine, quantify, or exploit the elastic moduli of cells. Combining mechanical tunability with the ability of cells to recognize and bind to the microbeads after protein coating make it possible to investigate the mechanosensitive responses seen in 2D culture in 3D microtissue culture/scaffold systems. In the application herein, the terms microbead, microparticle, microsphere, cell mimicking microparticles (CMMPs) and hyper compliant polymer particles are used interchangeably.

Mechanical properties of cells and their substrates have recently been recognized as important characteristics to consider for tissue engineering applications. With respect to intrinsic cell properties, the mechanical properties of undifferentiated adipose-derived stem cells (ASCs) have recently been correlated with their lineage-specific differentiation potential (Gonzalez-Cruz, R. D et al. *Proc Natl Acad Sci USA,* 2012 109(24):E1523-E1529). Normal human fibroblasts have been reported to mimic the mechanical properties of their substrates when cultured on two-dimensional (2D) polyacrylamide (PAAm) gels with varying elasticities (Solon, J. et al. *Biophysical Journal* 2007, 93(12):4453-4461). Additionally, substrate stiffness has been shown to induce stem cell differentiation for particular lineages (Engler, A. J. et al. *Cell* 2006, 126(4):677-689).

Though mechanical properties have been accepted as having implications in cellular morphology, gene expression, and fate, research in this area has been largely restricted to 2D culture platforms (Engler, A. J. et al. *Cell* 2006, 126(4):677-689; Yeung, T. et al. *Cell Motility and the Cytoskeleton* 2005, 60(1):24-34). However, three-dimensional (3D) culture systems are more biologically relevant for tissue engineering applications than traditional 2D culture because 3D culture systems better mimic in vivo microenvironments of living tissue (Achilli, T. M. et al. *Expert Opinion on Biological Therapy* 2012, 12(10):1347-1360). One such system, 3D spheroid culture, involves seeding cells into a non-adherent environment to promote intercellular interactions and the self-assembly of spheroids/aggregates (Napolitano, A. et al. *BioTechniques* 2007, 43(4): 494-500). This method maximizes the number of cell-cell contacts formed and allows for easier harvesting of cells for analysis compared to other common 3D culture systems, such as porous scaffolds or cell encapsulation (Kumachev, A. et al. *Biomaterials* 2011, 32(6):1477-1483; Loh, Q. L. Tissue Engineering Part B: Reviews 2013, 19(6):485-502). Previous studies have reported that stem cells cultured in 3D spheroids exhibited enhanced differentiation potential/stemness compared to stem cells cultured in 2D (Baraniak, P. R. et al. *Cell and Tissue Research* 2011, 347(3):701-711; Cheng, N. C. et al. *Stem Cells Translational Medicine* 2013, 2(8):584-594).

Culture systems which are 3D are a powerful tool for examining more physiologically relevant models with some limitations. One limitation of spheroid cultures is poor diffusion of oxygen and nutrients in the culture medium to various depths of the spheroid (Cesarz, Z. et al. *Stem Cells. Stem Cells International* 2016, 1-11). With regard to stem cell differentiation, chemical induction factors may not penetrate as fully or uniformly through the spheroid, resulting in a radially heterogeneous differentiation response in spheroid cultures (Baraniak, P. R. et al. *Cell and Tissue Research* 2011, 347(3):701-711). One way this heterogenous/incomplete diffusion in spheroid cultures has been reversed is through the incorporation of synthetic microbeads into 3D spheroids. Some publications employing this technique reported more homogenous differentiation responses and improved metabolic functions (Bratt-Leal, A. M. et al. *Biomaterials* 2011, 32(1):48-56; Hayashi, K. et al. *Acta Biomaterialia* 2011, 7(7):2797-2803; Yamada, M. et al. *Lab Chip* 2015, 15(19):3941-3951). Though several publications investigate the behavior of stem cells in spheroidal cultures, delivery of stable, cell-like mechanical cues to stem cells in 3D spheroidal culture systems has not been reported.

In the examples herein, the changes in adipogenic differentiation response of adipose-derived stem cells (ASCs) in 3D spheroid culture as a result of the presence of passively incorporated, mechanically distinct populations of PAAm microparticles as well as soluble, lineage-specific induction factors were examined. In the examples herein microbeads were coated with collagen type-I to promote passive incorporation into the spheroids through cell recognition, in the form of integrin binding, to present stable mechanical cues to cells throughout the spheroid. Changes in the mechanical properties of whole spheroids were analyzed with atomic force microscopy (AFM). Changes in adipogenesis were analyzed by measuring the expression of the lineage-specific genes peroxisome proliferator-activated receptor gamma (PPARG), considered the "master regulator" of adipogenesis, and fatty acid binding protein 4 (FABP4), a more downstream gene, with qPCR over a 3-week induction period with mechanical and chemical differentiation signals (Bernlohr, D. A. et al. *Annu. Rev. Nutr.* 1997, 17:277-303; Rosen, E. D. et al. *Cell Biology* 2006, 7(12):885-896). AFM was used to characterize the temporal changes in the mechanophyenotype of 3D ASC spheroids due to the presence of chemical induction factors and passively incorporated PAAm microbeads, which served as stable, cell-sized mechanical cues. The effect of these soluble factors and mechanical cues was observed to have altered the endpoint expression of the adipogenic-specific genes, PPARG and FABP4.

Adipogenically differentiating ASCs in spheroidal cultures were observed to alter their mechanophenotype in response to the stiffness of passively incorporated microbeads. After 21 days in culture, the elastic moduli of 10 kPa composite spheroids were observed to be significantly higher than those with 0.25 kPa microbeads. Because no differences in the elasticity of 0.25 and 10 kPa composite spheroids were observed at early time points, these changes are due to cells responding to the elasticity of incorporated microbeads. Though there were no significant differences in the elastic moduli of spheroids containing about 1 kPa or 2 kPa microbeads, however, average composite spheroid elasticity was positively correlated with microbead stiffness. Chemical induction factors promote actin depolymerization, and adipogenic 10 kPa composite spheroids were observed to be more contractile and exhibited increased actin staining compared to other adipogenic composite spheroids.

Composite spheroids containing 0.25 kPa microbeads were observed to display no significant differences in elastic moduli between adipogenic and control media environments by the end of the 21-day induction period. Despite the similar mechanophenotypes of 0.25 kPa samples across media environments, the expression of PPARG and FABP4 was significantly upregulated for all spheroids cultured with induction factors compared to controls. The similar mechanophenotype of spheroids containing 0.25 kPa microbead indicates that this mechanical cue induced a more adipogenic-like phenotype of ASCs in spheroidal cultures. Soluble induction factors generated a far greater response in regard to gene expression. Changes in these adipogenic mRNA sequences may also occur at different rates for mechanical and chemical cues such that cells respond to microbead elasticity, continuing on a much longer timescale than with soluble induction factors.

Composite spheroids containing microbeads with elastic moduli greater than or equal to typical ASCs (>1 kPa), were observed to begin dissociating after two weeks in the absence of soluble, adipogenic induction factors. This dissociation is likely due to the ASCs preferentially binding to one another in presence of substrates of lower elasticity than the cells themselves, encouraging cell-cell interactions over cell-substrate interactions. Additionally cells can upregulate actin polymerization in the presence of stiffer mechanical cues. This can result in a strong spreading response on stiffer microbeads, and cells presented with more compliant substrates do not increase actin polymerization and remain more spherical and less contractile. This model is supported by the results in examples herein from the 2D PAAm gels, in which control samples spontaneous formed spheroids on 0.25 kPa gels but spread on stiffer substrates. This strong spreading/contraction may be powerful enough to sever cell-cell connections, ultimately leading to the dissociation of the spheroid.

Changes in spheroid size and opacity were observed to indicate viability, cell density and contraction of the spheroids. Smaller spheroids were either opaque, signifying a high cell density and spheroid contraction, or appeared lighter in color, signifying spheroid dissociation. Cell dense, contractile spheroids were observed to have higher elastic moduli compared to dissociating spheroids of similar size, which were observed to contain fewer cells. The steep decrease in the elastic modulus of the dissociating composite spheroids containing stiffer (>1 kPa) microbeads in control medium was observed to be due to the lower cell densities that leave the spheroids a loosely bound collection of microbeads that can slide past one other, offering little mechanical integrity. Adipogenic medium was observed to promote spheroid viability, allowing for cell-cell adhesions to persist even in the presence of stiffer microbeads. The persistence of the cell-cell interactions was observed to produce more stable spheroids that exhibited higher elastic moduli.

Despite measurable changes in spheroid diameters and mechanophenotypes, differences observed in lineage-specific gene expression due to incorporated microbead stiffness after 21 days in culture were minimal. For adipogenically-differentiating ASCs obtained from a single donor, 2D and 3D samples of matched substrate stiffness were observed to exhibit similar expression levels of both lineage-specific mRNA sequences within a single media condition. These data indicate that chemical induction factors are more significant than potential enhancement from mechanical cues in both 2D and 3D culture systems. A minor upregulation of FABP4 expression in 10 kPa composite spheroids was observed compared to 0.25 kPa samples in adipogenic medium. This upregulation is observed because of an increase in the diffusion of induction factors. The presence of stiffer microbeads promotes cell-bead over cell-cell interactions. This property renders to stiffer microbeads more effective as spacers because cells are unable to exert forces capable of deforming them. Additionally, cell-only spheroids were observed to exhibit higher relative expression of the adipogenic genes compared to those presented with microbeads in either medium environment. The lower relative expression of lineage-specific genes in composite compared to cell-only spheroids is due to upregulated metabolic activity, known to occur when microbeads are incorporated into spheroids (Hayashi, K. et al. *Acta Biomaterialia* 2011, 7(7):2797-2803). Since the lineage-specific mRNA expression was normalized to GAPDH, a gene involved in metabolic processes, this increase in metabolic activity may have artificially lowered the relative lineage-specific mRNA expression in composite spheroids. Additionally, cell-only samples do not interact with collagen type-I, which may attenuate adipogenic differentiation responses of the ASCs by encouraging actin polymerization (Whelan, M. C. *Journal of Biological Chemistry* 2002, 278(1):327-334).

Cell-only and 0.25 kPa spheroids were observed to exhibit minor upregulation of PPARG after 21 days in control medium compared to the other microbead conditions as well as their paired 2D samples. Since PPARG is an early adipogenic gene and no differences were observed in the expression of FABP4, a more downstream gene, it is possible that the ASCs in these samples may be entering the early stages of adipogenesis despite the lack of chemical cues (Bernlohr, D. A. et al. *Annu. Rev. Nutr.* 1997, 17:277-303; Rosen, E. D. et al. *Cell Biology* 2006, 7(12):885-896). The early upregulation of PPARG can also explain the similar levels of expression between 2D and 3D adipogenic samples, independent of mechanical cues. The similar endpoint expression of PPARG indicates that the expression of this gene reached a plateau after three weeks of exposure to chemical induction factors and that mechanical cues did little to further upregulate this gene.

ASCs in 3D spheroids typically were observed to exhibit higher expression of adipogenic genes than paired 2D cultures. This indicates that the morphology adopted by cells in spheroid cultures is more optimal for adipogenic differentiation than 2D cultures, despite greater availability of soluble factors in monolayers. Spheroidal culture may enhance adipogenic responses of ASCs by promoting more rounded morphologies with lower aspect ratios, characteristics of adipogenically differentiating stem cells (Kilian, K. A. et al. *Proceedings of the National Academy of Sciences* 2010, 107(11):4872-4877; McBeath. R. et al. *Developmental Cell* 2004, 6:483-495).

Time lapse imaging of initial spheroid formation showed that cells bind to coated microbeads almost immediately to form small aggregates around the beads. Multiple cell-microbead aggregates then coalesce and contract to form a composite spheroid. During the initial five-hour formation, the microwells seeded with only cells yielded spheroids similar in size to composite spheroids formed with all varieties of microbeads. Since particle number was kept constant, this indicates that the microbead populations of all stiffnesses were reasonable volumetric mimics of the ASC population. After the initial five hours of spheroid formation, cells appear to migrate towards the exterior of the spheroid, sequestering microbeads to the spheroid center over the next 24-48 hours. This migration may be due to the relatively higher abundance of nutrients towards the perimeter of the spheroid, an active response to create a basal layer of collagen, or simply where forces on the microbeads reach an equilibrium since similar numbers of cells would exert forces from all sides.

The application herein provides a method of by which stable mechanical cues are delivered to human ASCs in 3D spheroid culture using collagen type-I-coated, PAAm microbeads. The mechanical properties of cell-only and composite spheroids, containing microbeads with distinct elastic moduli, were characterized using AFM over three weeks of culture with and without soluble, adipogenic induction factors. Spheroids were observed to respond to the stiffness of incorporated microbeads, illustrated by the positive correlation of composite spheroid mechanophenotype to microbead elasticity. Composite spheroids containing microbeads of greater than 1 kPa exhibited dissociation when cultured without adipogenic induction factors, likely due to ASCs preferentially binding to microbeads over neighboring cells. The most compliant, 0.25 kPa microbeads were observed to yield composite spheroids that exhibited elasticities and sizes most closely resembling the cell-only adipogenic spheroid when cultured with or without soluble, chemical cues. These data indicate that the compliant microbeads were able to induce a more adipogenic-like mechanophenotype even absent chemical factors. However, these low-elasticity cues yielded minimal upregulation of adipogenic-specific mRNA sequences compared to stiffer microbead conditions in either media environment. More measurable changes in lineage-specific gene expression are expected to arise if microbeads were more homogeneously distributed throughout composite spheroids. Additionally, assessing gene expression at earlier and/or more frequently for samples provided both chemical and mechanical cues could reveal potential temporal enhancement in the differentiation response. Various protein coatings and seeding ratios are used to optimize the delivery of mechanical cues in this type of culture system for potential tissue engineering applications.

Recent research has focused on creating microparticles that resemble aspects of living cells, termed cell mimicking microparticles (CMMPs), to improve their performance in regenerative medicine, drug delivery, and basic research systems. CMMPs have been fabricated to mimic the mechanical, topographical, and morphological characteristics of cells, and can be further modified to recapitulate the surface coatings of cells or their release of biological compounds. These types of particles can serve as scaffolds and stimulants for use in three-dimensional (3D) culture systems. Even though two-dimensional mimicking strategies have had success (Lopez-Fagundo, C. et al. *Acta Biomater* 2016, 39: 55-64; Bruder, J. M. et al. *Langmuir* 2006, 22(20): 8266-70), tissue constructs organized as a 3D structure allow for more cell-cell contacts compared to monolayer culture, providing special advantages by using compliant materials that are known to influence stem cell differentiation (Baraniak, P. R. et al. *Cell and Tissue Research* 2011, 347(3): 701-711; Cheng, N. C. et al. *Stem Cells Translational Medicine* 2013, 2(8): 584-594; Gao, L. et al. *Stem cells* 2010, 28(3): 564-72; Tang, J. et al. *Biomaterials* 2010, 31: 2470-2476; Marie, P. J. et al. *BoneKey reports* 2013, 2: 330).

Though several studies have used microparticles to investigate stem cell differentiation in 3D, their performance and integration with cultured constructs do not mimic aspects of living cells. CMMPs are designed to simulate cell characteristics such as surface proteins, mechanical properties, morphology, size, and/or secreted factors, eliciting the beneficial effects of live-cell therapies, in regard to tissue regeneration (Bratt-Leal, A. M. et al. *Biomaterials* 2011, 32(1): 48-56; Hayashi, K. et al. *Acta Biomaterialia* 2011, 7(7): 2797-2803; Kiser, P. F. *Nature* 1998, 394(6692): 459-462; Stidler, B. et al. *Advanced functional materials* 2011, 21(1): 14-28; Labriola, N. R. et al. *Biomaterials science* 2017, 5(1): 41-45; Tang, J. et al. *Nat Commun* 2017, 8: 13724). CMMPs with these characteristics have demonstrated improved incorporation into 3D microtissue constructs as well as the ability to alter the gene expression and cytoskeletal arrangements of cells, allowing for moderate control of cell behavior and lineage-specific differentiation responses.

Applications of CMMPs extend to regenerative medicine, cryogenic cell preservation, drug delivery, and diagnostic systems. Some modifications, such as surface coatings and mechanical property tuning, which can improve tissue-specific targeting and penetration into tissues or cells, can enhance drug delivery or screening. More generally, CMMPs are useful calibration and test particles in devices that manipulate, characterize, retain, or pass-through cells, as they more accurately replicate cellular adhesive and deformation behavior compared to unmodified, rigid particles.

Microparticles have been reviewed with regard to drug delivery and tissue engineering applications (Lee, K. et al. *J R Soc Interface* 2011, 8(55): 153-70; Panyam, J. et al. *Advanced Drug Delivery Reviews* 2003, 55(3): 329-347; Sokolsky-Papkov, M. *Adv Drug Deliv Rev* 2007, 59(4-5): 187-206). This application provides particles designed to mimic the properties of cells through modifications of fabrication procedures, advantages of these particles compared to conventional techniques. The application herein further provides methods for fabrication and customization techniques for regenerative medicine, drug delivery, cell preservation, and diagnostic applications with respect to cell mimicking strategies.

CMMPs can serve as tools for regenerative medicine/tissue engineering therapies, enhancing drug screening/delivery, monitoring intratissue stresses and strains, and elucidating the behavior of cells in flow-based devices. As each application requires different CMMP design parameters, a range of fabrication methods provides advantages for creating the ideal particle for each specific use.

Regenerative Medicine

CMMPs are used in regenerative medicine research as a unique scaffold that can deliver multiple signals to surrounding cells in a controlled fashion. The initial studies in this art coated poly (lactic-co-glycolic acid; PLGA) nanoparticles with cell membranes from red blood cells (Luk, B. T. et al. *Nanoscale* 2014, 6(5): 2730-7), platelets (Hu, C. M. et al. *Nature* 2015, 526(7571): 118-21; Hu, C. M. *Proc Natl Acad Sci USA* 2011, 108(27): 10980-5), bone marrow stem cells and smooth muscle cells (Toledano Furman, N. E. et al. *Nano Lett* 2013, 13(7): 3248-55), leukocytes (Parodi A, et al. *Nat Nanotechnol* 2013, 8(1): 61-8), and even cancer cells (Fang, R. H. et al. *Nano Lett* 2014, 14(4): 2181-8), to mimic the surface characteristics of these cell types. Tang et al. describes mimicking the surface proteins and secretome of cardiac stem cells by attaching portions of their plasma membranes to PLGA microparticles, as well as incorporating cell secreted proteins into the polymer network during the fabrication process (Tang, J. et al. *Nat Commun* 2017, 8: 13724).

Microparticles in general have been utilized to address key issues of 3D tissue constructs, such as limited diffusion caused by the lack of vasculature and formation of gap junctions at cell-cell contacts—an issue that can complicate the delivery of nutrients and chemical induction factors through the extracellular space of these constructs (Bratt-Leal, A. M. et al. *Biomaterials* 2011, 32(1): 48-56; Hayashi, K. et al. *Acta Biomaterialia* 2011, 7(7): 2797-2803). Microparticles have also been doped with growth factors or drugs to controllably deliver these factors to cells that would otherwise be more isolated deep within the microtissues (Kiser, P. F. *Nature* 1998, 394(6692): 459-462; Stidler, B. et al. *Advanced functional materials* 2011, 21(1): 14-28). Loading microparticles with cargo yielded improved differentiation responses and regenerative capacities compared to blank microparticles by providing more direct delivery of soluble factors (Peter, S. J. et al. *J Biomed Mater Res.* 2000, 50(3): 452-462; Basmanav, F. B. et al. *Biomaterials* 2008, 29(31): 4195-204; Park, H. et al. *Biomaterials* 2007, 28(21): 3217-27).

Researchers describe affecting cell behavior by controlling external stimuli that dictate cellular adhesion, migration, proliferation, morphology, gene expression, and differentiation in 3D, biomimicking environments to produce tissue constructs for implantation or promote the regeneration of existing tissues (Gao, L. et al. *Stem cells* 2010, 28(3): 564-72; Tang, J. et al. *Biomaterials* 2010, 31: 2470-2476; Tang, J. et al. *Nat Commun* 2017, 8: 13724; Dado, D. et al. *Seminars in cell & developmental biology* 2009, 20(6): 656-64; Dutta, R. C. et al. *Biotechnology advances* 2009, 27(4): 334-9; Dutta, R. C. et al. *Biotechnology advances* 2010, 28(6): 764-9; Engler, A. J. et al. *Cell* 2006, 126(4): 677-689; Hollister, S. J. et al. *Nature Materials* 2005, 4: 518-590; Kumbar, S. G. et al. *Biomedical materials* 2008, 3(3): 034002; Parekh, S. H. et al. *Biomaterials* 2011, 32(9): 2256-64).

The CMMPs herein provide a new approach to delivering cues capable of directing stem cell fate and addressing limitations of current tissue engineering practices. CMMPs herein were designed to match the size, morphology, surface coatings/roughness, mechanical properties, and protein release profiles of cells, which allow for their passive incorporation into microtissue constructs, during or after their self-assembly, to directly influence the behavior and biology of surrounding cells (Labriola, N. R. et al. *Biomaterials science* 2017, 5(1): 41-45 incorporated herein by reference; Doshi, N. et al. *Proc Natl Acad Sci USA* 2009, 106(51): 21495-9; Lautscham, L. A. et al. *Biomaterials* 2014, 35(10): 3198-207; Yamada, M. et al. *Lab Chip* 2015, 15(19): 3941-3951). From a practical perspective, CMMPs are compatible with fluorescent stains, making them an incredibly versatile tool for tissue engineering applications and general research (Labriola, N. R. et al. *Biomaterials science* 2017, 5(1): 41-45 which is hereby incorporated by reference herein in its entirety). CMMPs can be loaded with drugs or therapeutics and tuned to have specific release profiles for administering treatments to damaged or diseased tissues via diffusion, post integration (Stidler, B. et al. *Advanced functional materials* 2011, 21(1): 14-28; Kozlovskaya, V. et al. *ACS nano* 2014, 8(6): 5725-5737; Han, Y. et al. *Joint Bone Spine* 2010, 77(1): 27-31). Compared to bulk biomaterials that encapsulate cells or rely on their infiltration into pores, neotissues composed only of cells and CMMPs allow for more natural formation of cell-cell and cell-CMMP contacts, making cell arrangement and interaction more dynamic than traditional scaffolds (Labriola, N. R. et al. *Biomaterials science* 2017, 5(1): 41-45 which is hereby incorporated by reference herein in its entirety). As shown in Examples herein, CMMPs can be designed to mimic the size and mechanical properties of stem cells for incorporation into self-assembled cell spheroids (see also Labriola, N. R. et al. *Biomaterials science* 2017, 5(1): 41-45), as well as the size, shape, and stiffness of red blood cells to investigate how they move through capillary-like channels (Doshi, N. et al. *Proc Natl Acad Sci USA* 2009, 106(51): 21495-9; Kozlovskaya, V. et al. *ACS nano* 2014, 8(6): 5725-5737; Merkel, T. J. et al. *Proc Natl Acad Sci USA* 2011, 108(2): 586-91).

Early CMMPs have shown promise for improving tissue-based therapies, however there is a need for combining surface coatings, mechanics, drug loading, morphological control of these particles, and incorporation of artificial gap junctions to promote networked communication among cells attached to intervening microparticles.

Drug Delivery

Micro-sized particles and nano-sized particles have long been the primary approach for drug delivery purposes, though only recently have properties such as surface coatings and mechanical properties been taken into consideration for improving aspects such as tissue-specific accumulation and circulation time. By loading microparticles with biological compounds, these systems can mimic the release profiles of cells and organs, although they lack the feedback mechanisms that living cells possess (Stidler, B. et al. *Advanced functional materials* 2011, 21(1): 14-28; Han, Y. et al. *Joint Bone Spine* 2010, 77(1): 27-31). The characteristics of the particles are integral to how an organism interacts with them. Particle size and morphology also play important roles in their tissue distribution (Decuzzi, P. et al. *J Control Release* 2010, 141(3): 320-7). For example, the number of spherical particles in a given tissue/organ will decrease monotonically as size increases; however, a disproportionate fraction of particles will always accumulate in the reticuloendothelial system organs (Desai, M. P. et al. *Pharm Res* 1996, 13(12): 1838-45; Juliano, R. L. et al. *Biochem Biophys Res Commun* 1975, 63(3): 651-8). Discoidal particles have been observed to accumulate in most tissues to a greater extent than spherically, quasi-hemispherically, or cylindrically shaped particles. With respect to intracellular delivery, rod-shaped particles have been observed to undergo increased phagocytosis as compared to spherical microparticles (Champion, J. A. et al. *Pharm Res* 2009, 26(1): 244-9). These alternative shapes are particularly relevant to CMMPs that replicate unique cell types like discoidal red blood cells. Particle size is also integrally related to the loading and encapsulation efficiency of drugs, with greater efficiency correlating with larger particles.

As with past particle-based drug delivery approaches, chemically loaded CMMPs typically exhibit a burst release of their cargo (Huang, X. et al. *J Control Release* 2001, 73(2-3): 121-36), although through modifications, a controlled/sustained release is possible (Langer, R. et al. *Nature* 1976, 263(5580): 797-800). Alternatively, drug-eluting nanoparticles that release therapeutics in a controlled manner can be fully encapsulated within CMMPs, which would act as a delivery vehicle. The strategies currently used to accumulate drug delivering microparticles in a specific organ or area can also be applied to CMMPs (Kamaly, N. et al. *Chem Soc Rev* 2012, 41(7): 2971-3010). These types of drug delivery systems are often intended for use in cancer treatment and target the diseased tissues through an enhanced permeability and retention effect, mainly through size-based mechanisms (Luo Y, Prestwich G D, Cancer-targeted polymeric drugs. *Curr Cancer Drug Targets* 2002, 2(3): 209-26; van Vlerken, L. E. et al. *Expert Opin Drug Deliv* 2006, 3(2): 205-16).

Integration of various ligands on the surface of microparticles is another means of accomplishing targeted delivery and has been demonstrated with $\alpha_v\beta_3/\alpha_v\beta_5$ integrin-binding RGD peptides (Suh, W. et al. *Mol Ther* 2002, 6(5): 664-72), as well as alendronate and aspartic acid peptides (Wang, D. et al. *Bioconjug Chem* 2003, 14(5): 853-9). Another component to consider for CMMP-based, drug delivery applications is circulation time. The circulation time of both polymeric and liposomal microparticles has been increased by adding polyethylene glycol (PEG) to the surface or altering the mechanical properties and size of the particles. The enhanced retention/circulation time is attributed to the fact that PEGylation reduces renal clearance (Harris, J. M. et al. *Clin Pharmacokinet* 2001, 40(7): 539-51), which in turn may affect cellular uptake and intracellular trafficking (Mishra, S. et al. *Eur J Cell Biol* 2004, 83(3): 97-111). A goal of research in formulations is to produce microbeads having highly compliant mechanical properties and coatings that disguise particles as native cell types.

Diagnostic Tools

Potential applications of CMMPs include use as calibration or test particles for flow cytometry and microfluidic devices, force measurement probes, and tools for toxicology screening, among other possibilities. Systems that involve cells could substitute CMMPs for preliminary testing purposes. Particle sizers, automated cell counters, flow cytometry, and fluorescence activated cell sorting (FACS) are common techniques used to analyze or sort cell populations through the detection of fluorescence or light scattering to determine either the presence of specific proteins/genes or the size and complexity of the cell/particle passing through an interrogation point (Herzenberg, L. A. et al. *Clinical Chemistry* 2002, 48(10): 1819-1827). These devices are a regular tool for the assessment of stem and other cell types.

However, the polystyrene and latex particles used to calibrate these systems exhibit mechanical moduli 5-6 orders of magnitude higher than those of living cells, resulting in substantially different deformation behavior when flowing at high speeds in small channels (Chandler, W. L. et al. *J Thromb Haemost.* 2011, 9(6): 1216-24; Mullier, F. et al. *J Thromb Haemost.* 2011, 9(8): 1679-81, author reply 1681-2). CMMPs that are mechanically matched to cells provided herein are more similar to cells in regard to their locations in streamlines, deformation/elongation, and rotation in flow. These highly compliant particles vastly improve the utility of forward and side scatter (FSC and SSC) measurements, providing a more accurate assessment of cell size in these ubiquitous devices. More generally, use of CMMPs as a stable, off-the-shelf substitute for cells in product testing could potentially save significant time and money normally devoted to maintaining and handling biohazardous cell cultures.

Microfluidic devices are another tool being developed to characterize and/or sort cells for high-throughput assessment of cell populations or the detection of rare cell types (Gossett, D. R. et al. *Analytical and bioanalytical chemistry* 2010, 397(8): 3249-67; Hur, S. C. et al. *PloS one* 2012, 7(10): e46550; Hur, S. C. et al. *Lab Chip* 2011, 11(5): 912-20). Such devices have potential applications in cancer/rare cell diagnostics, general research purposes, and cell-based medicine. The mechanophenotype of cells has been recognized as a biomarker that correlates with the metastatic potential of cancer cells (Xu, W. et al. *PloS one* 2012, 7(10): e46609) and the lineage-specific differentiation potential of stem cells (Gonzalez-Cruz, R. D. et al. *Proc Natl Acad Sci USA* 2012, 109(24): E1523-E1529). As such, microfluidic devices that characterize and sort cell populations by their mechanical properties can be used for cancer diagnostics or to isolate subpopulations of stem cells with the greatest potential for the desired tissue type, potentially resulting in major improvements to current tissue engineering techniques that utilize more heterogeneous cell populations. With respect to flow cytometry or FACS calibration particles that closely resemble the characteristics of cells are advantageous over non-deformable particles for modeling cellular behavior in these types of flow fields. CMMPs provided herein could substitute for cells during pilot work, optimization of flow rates, and determination of device accuracy and precision. Particles used for this purpose should be very stable and therefore should not utilize biodegradable materials to minimize potential changes in mechanical properties and size.

Examples herein demonstrate that hyper-compliant CMMPs (<1 kPa) deform substantially within microtissue constructs in response to the contractile forces of surrounding cells (FIG. 15A; Labriola, N. R. et al. *Biomaterials science* 2017, 5(1): 41-45, incorporated herein by reference). Since the material properties of CMMPs can be tightly controlled, it is feasible for them to be used as a tool for measuring intratissue forces that cells exert within 3D constructs. Such a tool can be used to probe changes in contractile forces generated by cells within microtissues resulting from changes in the lineage commitment of stem cells, metastatic potential of cancer cells, or changes in cadherin/integrin binding and cytoskeletal structures resulting from drug treatments. This technique provides force measurements from within complex microtissues, an advantage over other mechanical characterizing techniques such as AFM, and these measurements could also be obtained from fluorescent images without the use of more expensive and complicated equipment. Complex morphologies would likely complicate the calculation of these forces, making simple, spherical particles advantageous for this type of application.

Additionally, CMMPs may be used as a tool for toxicology screening. CMMPs can be loaded with a drug of interest and delivered into microtissue constructs to test various doses or release profiles. This technique provides advantages over traditional toxicology experiments that use 2D culture systems or rely on diffusion of drugs/soluble factors through 3D tissue constructs by providing a high throughput platform that can deliver more information on the localized effects of the cargo within the more physiologically relevant 3D microtissue constructs (Baraniak, P. R. et al. *Cell and Tissue Research* 2011, 347(3): 701-711; Cesarz, Z. et al. *Stem Cells International* 2016, 2016: 1-11). Furthermore, the CMMPs can be fabricated to mimic smaller structures, such as a bacteria or other pathogens, to study phagocytic uptake by cells or macrophages to determine the effects of drugs as delivered directly to the cytosol.

Fabrication Methods

A variety of fabrication methodologies exist for producing microparticles and CMMPs, each with their own advantages and limitations (Table 1). Most of these fabrication techniques utilize polymers or fatty acids/amphiphilic materials (e.g. liposomes) to produce either homogenous spheres or core-shell structured microcapsules, respectively (Kumari, A. et al. *Colloids Surf B Biointerfaces* 2010, 75(1): 1-18). Self-assembly and phase separation are the driving mechanisms for many of these methods, including: solvent evaporation, emulsion polymerization and in situ/interfacial polymerization, salting-out, and phase inversion nanoencapsulation (Allemann, E. et al. *Pharm Res* 1993, 10(12): 1732-7; Barichello, J. M. et al. *Drug Dev Ind Pharm* 1999, 25(4): 471-6; Reis, C. P. et al. *Nanomedicine* 2006, 2(1): 8-21; Rosca, I. D. et al. *J Control Release* 2004, 99(2): 271-80).

Highly monodisperse particles with custom-designed morphologies can be produced using Particle Replication In Non-wetting Templates (PRINT); however, templates need to be entirely redesigned to produce particles of different morphology or size, which can be expensive and time consuming (Gratton, S. E. et al. *J Control Release* 2007, 121(1-2): 10-8; Rolland, J. P. et al. *J Am Chem Soc* 2005, 127(28): 10096-100). Another fabrication technique that allows for morphological control is layer-by-layer (LBL) deposition. This method involves depositing layers of a selected material on template seed particles that possess the desired morphology to produce shells that maintain the original, irregular shape (Park, J. H. *Acc Chem Res* 2016, 49(5): 792-800; Yan, Y. et al. *Chemistry of Materials* 2014, 26(1): 452-460). Once shell particles are obtained they can be porated and infiltrated with hydrogels to alter the material of the microparticles (Kaehr, B. et al. *Proc Natl Acad Sci USA* 2012, 109(43): 17336-41). Microfluidic/capillary-based approaches can form highly monodisperse populations of microparticles but are less high-throughput by the nature of their setups (Xu, S. et al. *Angewandte Chemie International Edition* 2005, 44(5): 724-728; Zhang, M. et al. *Particuology* 2016, 24: 18-31). Preparation techniques and self-assembly driven systems specific to liposomes are used to produce microparticles through: mechanical agitation (e.g., sonication, vortexing, micro fluidizers, French press, etc.), solvent replacement, detergent removal, size transformation, and fusion (Deamer, D. W. et al. I 1983: 27-51; Nii, T. et al. *Int J Pharm* 2005, 298(1): 198-205; Olson, F. *Biochim Biophys Acta* 1979, 557: 9-23; Riaz, M. *Pakistan Journal of Pharmaceutical Sciences* 1996, 9(1): 65-77; Szoka, F. Jr. et al. *Annu Rev Biophys Bioeng* 1980, 9: 467-508). Emulsion droplet size is controlled, most simply, by adjusting the level of mechanical agitation during production or through filtering once the particles are formed.

TABLE 1

Advantages and disadvantages of microparticle fabrication methods

| Technique | Pros | Cons |
| --- | --- | --- |
| Solvent evaporation | Scalable | Uses organic solvents |
|  | Easy to use | High polydispersity |
|  | Hydrophobic/hydrophobic encapsulation | Only Spherical particles |
| Emulsion polymerization and in situ/interfacial polymerization | Scalable | Uses organic solvents |
|  | Easy to use | Medium polydispersity |
|  | Good compatibility with high compliance materials | Only spherical particles |
| Salting out | Hydrophobic/hydrophilic encapsulation | Can disturb sensitive biologics |
|  |  | High polydispersity |
|  |  | Only spherical particles |
|  |  | Limited versatility |
| Phase inversion nanoencapsulation | Scalable | Uses organic solvents |
|  | Easy to use | Medium polydispersity |
|  | Hydrophilic encapsulation | Only spherical particles |
|  |  | Requires large volumes |
| Particle replication in non-wetting templates (PRINT) | High monodispersity | Low yields |
|  | Morphological control | Difficult to scale process |
|  | High loading/encapsulation efficiencies | Relatively complex |
| Layer-by-layer (LBL) | Morphological control | Low yields |
|  | High loading/encapsulation | Difficult to scale process |

TABLE 1-continued

Advantages and disadvantages of microparticle fabrication methods

| Technique | Pros | Cons |
|---|---|---|
|  | efficiencies<br>Both hydrophilic/hydrophobic encapsulation | Relatively complex |
| Micro/capillary fluidics | Easy to use<br>High monodispersity<br>High loading/encapsulation efficiencies | Low yields<br>Only spherical particles |

CMMP Customization

Polymer microparticles can be customized using techniques to more closely mimic additional properties of cells, including: morphology, surface molecules, protein secretions, mechanical properties, and more. The morphology of microparticles can be controlled through techniques that make use of templates, such as PRINT or LBL, through the careful design of microfluidic devices (Xu, S. et al. Angewandte Chemie International Edition 2005, 44(5): 724-728; Xu, Q. et al. Small 2009, 5(13): 1575-81), or through the physical modification of spherical microparticles produced by other methodologies (Ho, C. C. et al. Colloid & Polymer Science 1993, 271(5): 469-479; Champion, J. A. Proc Natl Acad Sci USA 2006, 103(13): 4930-4).

Surface molecules for CMMP coatings play a primary role in how the particle interacts with biological systems. From a delivery/homing standpoint, coatings can be used to extend circulation time (PEGylation) or allow targeting of specific cells/organs, e.g., by the addition of tissue-specific membrane receptors (Harris, J. M. et al. Clin Pharminacokinet 2001, 40(7): 539-51; Sudimack, J. et al. Adv Drug Deliv Rev 2000, 41(2): 147-162). In a broader sense, coating with cell adhesion molecules will allow for a range of CMMP-cell and CMMP-material interactions that would otherwise not occur with an inert polymer as described in examples herein (Labriola, N. R. et al. Biomaterials science 2017, 5(1): 41-45). Researchers can use this approach to investigate how specific integrins, cadherins, or other binding molecules influence the organization and movement of CMMPs within a cell-dense structure. This is a consideration for controlling the dispersion of CMMPs in tissues because it is observed that CMMPs have a tendency for collagen-coated particles to aggregate, at least in microtissue spheroids (FIG. 15B; Labriola, N. R. et al. Biomaterials science 2017, 5(1): 41-45). Alternatively, surface coatings can even be used to mimic cellular activity by encapsulating materials like enzymes that release as sacrificial outer layers degrade (Caruso, F. Langmuir 2000, 16(4): 1485-1488).

A key characteristic of cells is their mechanical properties. The vast majority of microparticles are made from rigid materials that are 5-6 orders of magnitude stiffer than a living cell. Examples herein demonstrate that hydrogel materials can be used to fabricate CMMPs exhibiting physiologically relevant sizes and elasticities (5-40 µm, 0.1-5 kPa, respectively; Labriola, N. R. et al. Biomaterials science 2017, 5(1): 41-45). Substrate material stiffness, in both 2D and 3D culture systems, dramatically influences stem cell morphology, mechanical properties, and differentiation response (Engler, A. J. et al. Cell 2006, 126(4): 677-689). Adjusting the crosslinking density of a polymer is the most prevalent means of tuning microparticle mechanical properties (Anseth, K. S. et al. Biomaterials 1996, 17(17): 1647-1657; Hasirci, V. et al. Bio-Med Mater Eng 2000, 10(1): 19-29).

Other possibilities include microparticle stiffness which is adjusted for LBL by controlling how many layers are deposited (Schneider, G. et al. Langmuir 2008, 24(5): 1778-89), and techniques that generate core/shell structures can choose shell materials with defined elastic moduli (Wang, Y. Nat Mater 2006, 5(10): 791-6; Jiang, X. et al. J Am Chem Soc. 2006, 128: 4512-4513). In general, most of these approaches are limited to use with high-modulus materials outside of the physiologically relevant range. Studies that modulate microparticle crosslinking do so to control the release rate of encapsulated drugs, rather than mimicking cellular properties (Zhu, Y. et al. Angew Chem Int Ed Engl 2005, 44(32): 5083-7). In this novel direction, hydrogel microparticles offer the best range of mechanical properties to achieve accurate mimics. Although hydrogel microparticles are not compatible with all fabrication techniques, these materials provide unique advantages in the area of biomechanics compared to other, primarily solid materials. Apart from directing cell behavior or altering molecular release kinetics, the mechanical properties of microparticles have also been shown to influence their uptake by cells and tissues as well as circulation and clearance time in an organism (Anselmo, A. C. ACS Nano 2015, 9(3): 3169-77). Stiffer particles exhibit increased uptake compared to their softer counterparts while the more compliant particles remain in circulation longer.

CMMPs are needed that mimic the cellular release of proteins, steroids, growth factors, and other compounds to elicit desired biological responses. Incorporating physiologically representative surface coatings and topography can promote active interactions with neighboring cells. Depending on the specific application, CMMP degradation is also a design factor as CMMPs should be biodegradable, lessening the chance of a negative, long-term response to any shed materials. Alternatively, use of CMMPs as calibration particles or general, cell substitutes for testing equipment would favor non-degrading materials that extend shelf-life and ease-of-handling.

Modifications to CMMPs include fluorescent staining and nanoparticle incorporation. A visual indicator, is better able to track particle movement, interactions with cells, deformation, or assist with detection in various devices such as flow cytometers. Such dyes can be incorporated through covalent bonding, hydrogen bonding, intercalation, etc., making them compatible with many different polymer types and fabrication methodologies. Nanoparticle incorporation can serve a variety of purposes, including degradative release of drugs, light refraction, and magnetic control. This type of modification is not compatible with all fabrication approaches since the pre-formed nanoparticles are typically doped in during the formation phase of the microparticles. The ultimate function can be similar to a coated, solid particle; however, there is often more versatility in being able to add a variety of function-specific nanoparticles within a larger CMMP.

To obtain CMMPs that can truly substitute for cells, methods herein are provided for incorporating surface modifications, nanoscale topographies, bulk mechanical properties, and size restriction, so that CMMPs can be optimized for use in regenerative medicine or as replicas that can calibrate devices, deliver drugs, and measure forces.

The invention having now been fully described, it is further illustrated by the following examples and claims, which are illustrative and are not meant to be further limiting.

A portion of this work was published in a paper entitled, "Fabricating polyacrylamide microbeads by inverse emulsification to mimic the size and elasticity of living cells", with co-authors and co-inventors, Nicholas R. Labriola, Edith Mathiowitz, and Eric M. Darling, Biomaterials science 2017; 5(1): 41-45 (published online Dec. 9, 2016) which is hereby incorporated by reference herein in its entirety.

A portion of this work has been submitted for publication to the journal, Stem Cells Translational Medicine as a manuscript entitled, "Fabrication, customization, and application of call mimicking microparticles in stem cells science" by co-authors Nicholas R. Labriola, Aharon Azagury, Robert Gutierrez, Edith Mathiowitz, and Eric M. Darling, which is hereby incorporated by reference herein in its entirety.

Example 1: Cell Culture

Human ASCs were isolated from the stromal vascular fraction of donated human lipoaspirate, obtained from the abdomen and thigh of a single, 56-year old, female, breast cancer patient using method described in Estes, B. T. et al. *Biotechnology and Bioengineering* 2008, 99(4):986-995. Prior to use in examples, ASCs were passaged three times in expansion medium consisting of DMEM/F-12 (Hyclone, GE Healthcare Life Sciences, Logan, UT), 10% fetal bovine serum (FBS, ZenBio, Research Triangle Park, NC), 1% antibiotic/animycotic (Hyclone), supplemented with 5 ng/mL epidermal growth factor, 1 ng/mL fibroblast growth factor, and 0.25 ng/mL transforming growth factor-β1 (R&D Systems, Minneapolis, MN; Estes et al. 2008).

For differentiation examples, cells were exposed either to adipogenic or control (stromal) medium. Control medium consisted of DMEM/F-12 supplemented with 10% FBS, and 1% antibiotic/antimycotic. Adipogenic medium consisted of control medium supplemented with 0.5 µM 3-isobutyl-1-methylxanthine, 10 µM insulin, 200 µM indomethacin, and 1 µM dexamethasone (Sigma-Aldrich, St. Louis, MO) (Zheng et al. 2006). Media was refreshed every two days for all examples and ASC expansion.

Example 2: Preparation of Mechanically Distinct Microbeads

Polyacrylamide (PAAm) bead populations with distinct elastic moduli, were fabricated, fluorescently stained, and coated with collagen by methods as follows to serve as stable, cell-sized, mechanical cues. PAAm solutions were prepared with phosphate buffered saline (PBS) made with ultra pure, Milli-Q water (18 MO resistivity, Merck Millipore, Billerica, MA), 0.1% of the initiators ammonium persulfate (APS, Sigma-Aldrich, Nantic, MA) and N,N,N',N'-tetramethylethylenediamine (TEMED, Thermo Fisher Scientific, Madison, WI, USA), and various concentrations of acrylamide (Bio-Rad, Hercules, CA) and the cross-linker, bis-acrylamide (Bio-Rad) to produce microbead populations with distinct elastic moduli. The PAAm formulations used in the examples herein included either 4% acrylamide with 0.05, 0.1 or 0.2% bis-acrylamide or 8% acrylamide with 0.3% bis-acrylamide. Microbead fabrication was achieved through vacuum-assisted (25" Hg) inverse emulsification in 200 mL of cyclohexane (HPLC grade, Thermo Fisher Sci.) containing 1% polysorbate 85 (Span 85, Sigma-Aldrich) within a 250 mL Erlenmeyer flask. For each microbead batch, 10 mL of one of the aforementioned PAAm formulations was introduced drop-wise into the stirring solvent/surfactant mixture and sheared into cell-sized droplets through vigorous agitation with a stir rate of 1500 RPM. Post-polymerization, microbeads were fluorescently stained with a rhodamine-derived dye (Sharpie, Oak Brook, IL) for improved visualization. Microbead surfaces were then activated through two sequential treatments of 0.5 mL of 1 mg/mL sulfo-SANPAH solution (CovaChem, LLC., Loves Park, IL) with a 15-minute exposure to ultraviolet (UV) light (The Southern New England Ultraviolet Co., Branford, CT), and subsequently functionalized with an overnight incubation in a 100 µg/mL rat tail collagen type-I (Millipore) solution at 4° C. on a shaker. The following day, 50 µL of 4 M HCl was added to the 5 mL collagen/microbead suspension to prevent collagen gelation, and the microbeads were pelleted with a five-minute, 1000 G centrifugation with the brake disabled. These centrifugation settings were used for all treatments to reduce the loss of microbeads due to resuspension caused by rapid deceleration. The 15 minute UV illumination serves also to sterilize beads, which are then manipulated under aseptic conditions.

Example 3: 2D Gel Preparation and Coating

Two-dimensional thin gels were produced to match the elastic moduli of each microbead population. Thin gels were observed to exhibit elastic moduli approximately 40-60% greater than microbeads produced from the same PAAm solution due to interactions with surfactant (Kronberg, B. et al. 2014. Surface Chemistry of Surfactants and Polymers. Hoboken NJ: John Wiley & Sons). As such, the bis-acrylamide concentrations in the PAAm solutions used for 2D gel fabrication were lowered so that the formulations consisted of either 4% acrylamide mixed with 0.06, 0.09, or 0.15% bis-acrylamide, or 8% acrylamide with 0.28% of the cross-linker. Gels were formed by pipetting a 75 µL droplet of each PAAm solution, containing 0.1% of APS and TEMED initiators, onto a chloro-silanated, hydrophobic glass slide, treated with hexane (Thermo Fisher Sci.), acetic acid (Thermof Fisher Sci.) and (tridecafluoro-1,1,2,2-tetrahydrooctyl) trichlorosilane (Gelest Inc., Morrisville, PA), and placing a circular, hydrophilic glass coverslip, treated with 3-aminopropyl-trimethoxysilane (Acros Organics, Thermo Fisher Sci.) and glutaraldehyde (Alfo Aesar, Thermo Fisher Sci.), on top of the droplet. After a 30-minute incubation at room temperature, the resulting gels were soaked in 1×PBS for 15 minutes. The PBS was changed three times to eliminate remaining monomers. The gels were then separated from the glass slides, remaining attached to hydrophilic coverslips, and transferred to 24-well plates where they were stored in PBS at 4° C. One day prior to cell seeding, the gels were coated with collagen through the same NHS ester cross-linking chemistry used with the microbeads. Each well was filled with 0.5 mL of 1 mg/mL Sulfo-SANPAH and the plates were exposed to UV light in a culture hood for 15 minutes. The fluid was then removed from each well and replaced with 0.5 mL of fresh sulfo-SANPAH solution for a second 15-minute UV exposure. Wells were then washed three times with PBS and allowed to equilibrate for at least 48 hours in stromal medium before cell seeding. The UV illumination sterilizes the gels, sending them free of viable pathogens.

Example 4: ASC, Microbead, and Gel Mechanical Characterization

The mechanical properties of ASCs and rhodamine-stained, collagen-coated PAAm microbeads of each formulation were characterized using an MFP-3D Bio atomic force microscope (AFM, Asylum Research, Santa Barbara, CA) using methods described in Darling, E. M. et al. *Osteoarthritis and Cartilage* 2006, 14(6):571-579. Samples were prepared using plasma treating coverslips in a corona discharge chamber (Harrick Plasma, Ithaca, NY) for two minutes. For ASC samples, cells were resuspended in stromal medium at a concentration of 1,000,000 cells/mL. A 100 μL droplet was then placed on a coverslip within a 50 mm, low-profile petri dish (Corning Inc., Corning, NY) and incubated for thirty minutes at 37° C. and 5% $CO_2$ for 30 minutes. Once cells were attached, the dishes were flooded with 3 mL of stromal medium for testing. For microbead populations, a 75 μL droplet of a 1,000,000 microbeads/mL solution was placed on the treated coverslip and sandwiched between a second, untreated coverslip. Microbeads attached to the coverslips were incubated for 15-minute at room temperature then the coverslips were soaked in PBS for thirty minutes and the treated coverslip containing adhered microbeads, was separated and moved to a 50 mm, low-profile petri dish and flooded with 3 mL of PBS for testing. The elastic moduli ($E_{elastic}$) of fifty individual microbeads from each PAAm formulation were obtained from force vs. indentation curves, acquired through single indentation tests performed with a silicon nitride cantilever (Bruker Corporation, MLCT10, k~0.03 N/m) tipped with a 5 μm polystyrene bead (Microbeads AS, Skedsmoorset, Norway), using a modified, thin-layer Hertz model (Dimitriadis et al. 2002). Indentations were completed using a 10 μm/s approach velocity and a 3 nN trigger force with the beaded probe of the cantilever positioned over the apex of each microbead. The same cantilever, approach velocity, and trigger force were also used in 2D gel testing. The elastic moduli of thin gels were quantitatively mapped using sixteen (4×4) indentations equally spaced over a 90×90 μm region. The average elastic modulus of the 2D gels was determined from force maps of three different regions of a gel fabricated from each formulation.

Example 5: Microbead Size Characterization

The size distribution of each microbead population was assessed through the analysis of epifluorescent images in ImageJ (U.S. National Institutes of Health, Bethesda, MD, version 1.47). The rhodamine-stained, collagen-coated microbeads from each stiffness group were diluted to 1,000,000 microbeads/mL, and 75 μL of the suspension was placed into a 24-well plate and covered with a circular coverslip. Nine images of the microbeads were acquired with a 10 Ox objective fit to a Nikon Eclipse Ti-U epifluorescent microscope (Nikon Instruments, Melville, NY) using a QICAM 12-bit digital camera (QImaging, Surrey, BC, Canada) and a DSRed filter cube (excitation: ~545 nm, emission: ~625 nm, Nikon Instruments) using an exposure time of 100 ms. Images were loaded into ImageJ and converted to a binary form through intensity thresholding followed by the "fill holes" feature. The "watershed" function was then applied to break up particles in contact with one another. The areas of individual microbeads (in pixels) were measured using the analyze particles tool with additional thresholding to detect only high intensity regions with areas larger than 5 pixels$^2$ and a circularity of greater and 0.80, ignoring illegitimate signals from background noise, irregularly shaped aggregates, or out of focus beads. The recorded pixel areas were then converted to microns using the pixel ratio of 2.12 pixels/μm, corresponding to the objective used, and effective circular diameters were calculated.

Example 6: 3D Spheroid Formation

Agarose microwells were used to provide a culture environment ideal for promoting intercellular interactions and self-assembly of spheroids. Microwells were cast from 3D Petri Dish® molds (#24-96-Small, Microtissues, Inc., Providence, RI) using molten, 2% agarose (Thermo Fisher Sci.). Microwells were cured with a 15-minute incubation at 4° C., transferred to 24-well plates, and equilibrated in stromal medium for 48 hours prior to introducing ASCs. Spheroid conditions consisted of either cells alone (115,000 cells) or with one of the mechanically distinct PAAm microbead formulations at a 1:1 ratio (cells:microbeads, 115,000 total particles). To prevent cells and microbeads from being flushed from the gels when introducing additional medium, freshly seeded microwells were incubated for 30 minutes at 37° C. and 5% $CO_2$ prior to flooding the wells with an additional 500 μL of either control or adipogenic medium. The microwells were seeded in triplicate to serve as biological replicates for qPCR lysates, and in triplicate again for mechanical characterization, with a harvesting single gel for characterization.

Example 7: Two-Dimensional Culture of ASCs

ASCs were seeded onto coverslips or collagen type-I-coated PAAm gels within 24-well plates at 80,000 cells/well. Phase microscopy images were acquired of ASCs after each of 1, 10, and 21 days of culture in each of adipogenic and control medium. Samples were produced in triplicate and sacrificed for lysates after Day 21 μmages were acquired at day 21.

Example 8: Spheroid Harvesting

Spheroids were harvested from agarose microwells to either prepare qPCR lysates or attach them to glass coverslips for mechanical characterization and confocal imaging. After spheroids were cultured for the appropriated time, agarose gels were removed from 24-well plates with a bent spatula and placed in a 50 mL conical tube. The gel was sliced in half and the spheroids were flushed from microwells by repeatedly pipetting 500 μL of stromal media over the gel at the base of the tube. Successful displacement from microwells was confirmed visually as spheroids could be seen by eye both within gels as well as floating in the medium. For qPCR lysate preparation, the resulting spheroid suspension was transferred to a 15 mL conical tube for centrifugation and subsequent digestion. For confocal imaging and AFM testing, the spheroid suspension was collected, placed in a droplet on a square coverslip in the center of a low profile AFM dish, and incubated for at least one hour at 37° C. to ensure spheroid attachment. If the spheroids appeared to be aggregating within the droplet they were agitated with a pipette prior to incubation. After the spheroids had attached to the coverslip, the dish was flooded with DMEM/F-12 and loaded onto the AFM for testing.

Example 9: Spheroid Mechanical Property Characterization

The elastic and viscoelastic properties of individual spheroids were characterized once a week for three weeks using an MFP-3D Bio AFM (Asylum Research) equipped with a 0.35 N/m silicon nitride cantilever tipped with a 25 µm polystyrene bead (Novascan Technologies, Inc., Boone, IA, PT.PS.SN.25). Once a week, fifteen spheroids for each microbead condition from both media environments were mechanically characterized. Spheroids cultured in each of adipogenic and control medium were tested on consecutive days for the first iteration of the example; this testing order was reversed for the second iteration. Tests were performed by positioning the cantilever over the center of each spheroid and performing a single indentation using a 10 µm/s approach velocity, 30-second relaxation period, and 30 nN trigger force. Data were analyzed using a custom MATLAB program.

Example 10: Lysate Preparation for qPCR

Lysates for qPCR analysis were obtained from each of 2D monolayers and 3D spheroids after 23 days in culture. ASCs grown on 2D PAAm gels were lysed by first aspirating the media from each well and a 15-minute incubation in 500 µL of TRIzol Reagent (Thermo Fisher Sci.) at room temperature. After incubation, the solution was pipetted repeatedly (at least about 10 times) over the coverslips/gels, and was transferred to a 1.5 mL tube. For 3D spheroid lysates, spheroids were harvested from gels the procedure described in examples herein. The spheroids were centrifuged in 15 mL conical tubes at 400 G for five minutes, the supernatant was aspirated, and the spheroids were resuspended in 500 µL of TRIzol. The suspension was then agitated by pipetting vigorously and transferred to a 1.5 mL snapcap tube. The TRIzol suspension was then incubated for 15 minutes at room temperature. Finally, all TRIzol lysate suspensions were vortexed and subsequently frozen at −80° C. for future analysis.

Example 11: Quantitative PCR

To verify successful adipogenic differentiation in ASCs in 3D spheroids and 2D PAAm gels, the expression of the lineage-specific genes PPARG and FABP4 was assessed by qPCR. mRNA was isolated from 2D and 3D ASCs cultured in each of adipogenic and control medium (N=3) on day 21 using QuickRNA Miniprep Kit (Zymo Research, Irvine, CA) in accordance with the manufacturer's guidelines. Isolated RNA (80 ng/reaction) was reverse transcribed using SuperScript II First Strand cDNA Synthesis Kit (Life Technologies, Waltham, MA). TaqMan Gene Expression Assay human primers (Life Technologies) for genes of interest PPARG, variant 2 (Hs00234592_m1) and FABP4 (Hs01086177_m1) in addition to the reference gene Glyceraldehyde 3-phosphate dehydrogenase (GAPDH; Hs03929097_g1) were used in all runs, and all samples were run in triplicate. Fluorescent signal was detected using a CFX96 Real-Time PCR Detection System (Bio-Rad, Hercules, CA) and was analyzed using the comparative delta Ct method (Silver et al. 2006). Relative PPARG and FABP4 expression was determined by normalizing to corresponding GAPDH expression.

Example 12: Spheroid Formation Timelapse

ASCs and rhodamine-stained, collagen-coated microbeads of each stiffness were suspended in stromal medium and seeded into equilibrated agarose microwells at a 1:1 ratio (cells:microbeads, 115,000 total particles), as described in examples herein. For the control conditions containing exclusively cells or uncoated, 1 kPa microbeads, a seeding density of 115,000 particles/gel was used to match particle numbers in composite spheroid conditions. For improved visualization, cells were fluorescently stained with calcein AM green (1 µg/mL, AnaSpec Inc., Fremont, CA) in stromal medium for 30 minutes at 37° C. and 5% $CO_2$. A five-hour time-lapse was generated with the automatic acquisition of brightfield, green-fluorescent, and red-fluorescent images at preset coordinated every fifteen minutes using a Carl Zeiss Axio Observer Z1 fitted with a 20× objective, an Xcite 120 XL mercury lamp (Exfo, Life Science Division, Mississauga, Ontario), and an AxioCam MRm camera (Carl Zeiss MicroImaging, Thronwood, NY). A custom incubation chamber was used to keep the sample a constant temperature and carbon dioxide concentration (37° C. and 10% $CO_2$) throughout the imaging session.

Example 13: Actin Staining/Confocal Imaging

Spheroids were harvested and attached to pre-mounted coverslips within low profile petri dishes (MatTek Corporation, Ashland, MA) as described in examples herein for the acquisition of confocal images. After spheroid attachment, the dish was washed three times with PBS and fixed overnight at 4° C. in 3 mL of 10% phosphate buffered formalin. Fixed samples were washed three times with (PBS) and stored at 4° C. for further processing. Prior to imaging, the cells within spheroids were permeabilized with a 30-minute incubation in 0.1% TritonX-100 (Sigma Aldrich) at room temperature. Following permeabilization, the actin structures of ASCs within spheroids were stained with a 30 minute incubation in a 0.165 µM solution of Alexa Fluor 488 Phalloidin (Molecular Probes, Thermo Fisher Sci., excitation: 495 nm emission: 518 nm). The samples were then washed with PBS and cell nuclei were subsequently stained with a thirty-minute incubation in a 0.1 µg/mL solution of 4',6-diamidino-2-phenylindole, dihydrochloride (DAPI, Molecular Probes, Thermo Fisher Sci.). The stained composite spheroids were then imaged using a Zeiss LSM 510 Meta Confocal Laser Scanning Microscope (Carl Zeiss Microscopy GmbH, Jena, Germany) in conjunction with an Axiovert 200M inverted microscope using Zeiss Efficient Navigation (ZEN) software version 2.1. Using a 40× objective, ~50 µm z-stacks of 1.33 µm slices were obtained for DAPI, visualized with a diode laser (405 nm), phalloidin, visualized with an Argon laser (488 nm) and microbeads, visualized with a Helium-Neon laser (633 nm).

Example 14: Statistical Analyses

To determine statistically significant differences between the spheroid mechanical properties and diameters, two-sample Kolmogorov-Smirnov non-parametric tests were performed with R statistical analysis software version 3.31 (R Core Team 2016, Vienna, Austria). For comparisons of relative gene expression levels of spheroids and 2D cultures, statistically significant differences were assessed with a Student's T-test. Comparisons were considered significant for p-values of less than 0.05. Measurements were considered outliers, and were subsequently removed from their corresponding data sets if they were more than 2.5 standard deviations from the mean.

Example 15: Fabrication of PAAm Microbeads

Figure 2A:
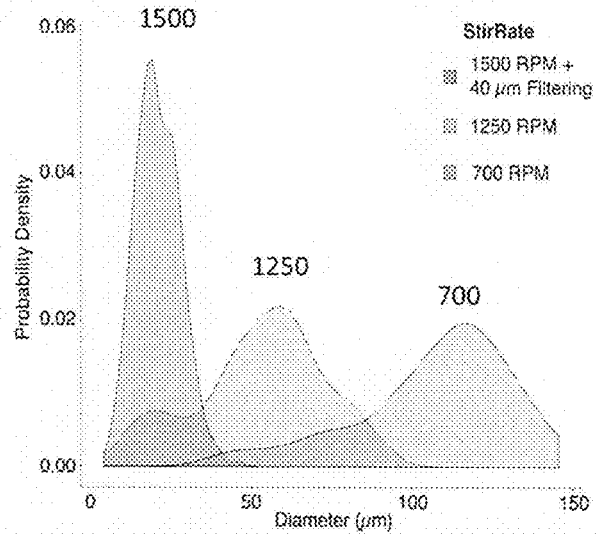
FIG. 2A and FIG. 2B are a graph and a set of microphotographs showing resulting microbead size distributions obtained using various stir rates.
Figure 2B:
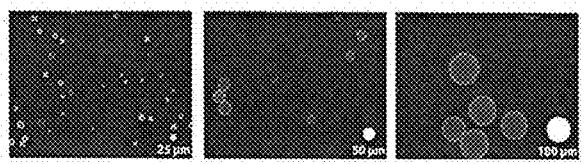

PAAm microbead fabrication was accomplished through inverse emulsion polymerization in a 250 mL Erlenmeyer flask using 200 mL of cyclohexane (HPLC grade, Thermo Fisher Scientific, Madison, WI, USA). The surfactant polysorbate 85 (Span 85, Sigma-Aldrich, Nantic, MA) was dispersed at a 1% (v/v) concentration in the cyclohexane solvent to stabilize microbeads in spherical morphologies and to minimize particle aggregation using a magnetic stirrer (375 Hotplate/Stirrer, VWR Scientific Products, Bridgeport, CT) with a cylindrical stir bar (39×10 mm, 2×11 mm pivot ring). Since free radicals are required to initiate the polymerization of PAAm, oxygen was removed from the system for synthesis to proceed uninhibited (Chrambach, A. et al. *Science,* 1971, 171(3982), 440-451). The solubility of dissolved gases was decreased by reducing the local environmental pressure with a vacuum pump (Battino, R. et al. *Chem. Rev.,* 1966, 66(4), 395-463). While stirring at 700 RPM, a −25" Hg vacuum was applied to the surfactant/solvent mixture for 30 minutes by linking a vacuum pump to the rubber stopper of the flask. An additional large volume vessel was connected in series between the pump and reaction vessel, and was additionally cooled, to condense any evaporated cyclohexane. During the degassing period, a 10 mL PAAm solution was prepared using acrylamide (Bio-Rad, Hercules, CA), bis-acrylamide (Bio-Rad), ammonium persulfate (APS, Sigma-Aldrich), and phosphate buffered saline (PBS, Thermo Fisher Sci.). PBS was prepared with ultrapure, Milli-Q water (18 MΩ resistivity, Merck Millipore, Billerica, MA). For the three formulations used in this examples, the final concentrations of acrylamide and APS were kept constant at 4% and 0.1%, respectively. The final concentrations of bis-acrylamide used were 0.05%, 0.1%, or 0.2% to create different levels of crosslinking and elasticity. Immediately after degassing, N,N,N',N'-tetramethylethylenediamine (TEMED, Thermo Fisher Sci.) was added to the PAAm solution to yield a final concentration of 0.1%. The mixture was vortexed for ten seconds and added drop-wise into the cyclohexane/Span 85 mixture. Vacuum was reapplied for one hour, and the stirring rate was increased to produce microbeads of the desired size. For this example, a stir rate of ~1500 RPM yielded a range of sizes similar to the ranges of typical mammalian cells (FIG. 2).

Figure 5:
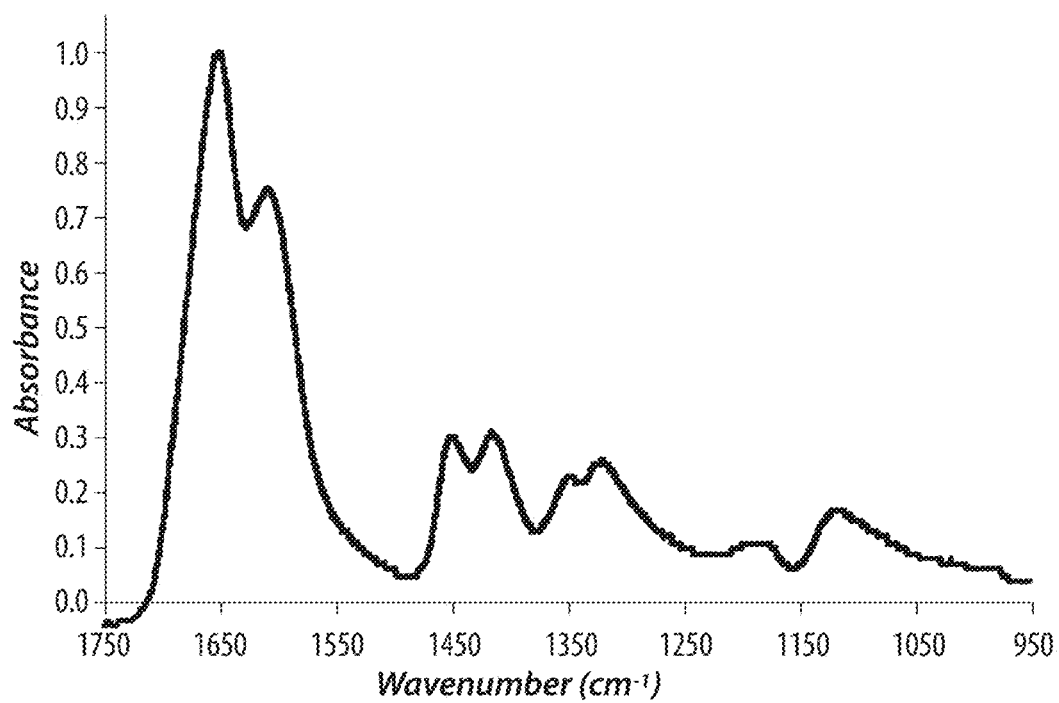
FIG. 5 is an attenuated Total Reflectance-Fourier Transform InfraRed (ATR-FTIR) absorbance spectrum of 0.1% bis-acrylamide microbeads. The spectrum of the fingerprint region demonstrates absorbance peaks at the expected wavenumbers for polymerized PAAm, corresponding to the flexural stretching of —NH bonds of both amide I and II (about 1613 cm-1), the C—N groups of both amides (about 1441, 1351, and 1281 cm-1), and the tensional stretching of the C=O groups of amide I (about 1675 cm-1).

Once polymerization was completed (about 1 hr), stirring was stopped, vacuum was released, the stir bar was removed, and microbeads were allowed to settle for 30 minutes. The solvent was removed, and the remaining solution containing microbeads (about 10 mL, viscous white fluid) was split between two, 50 mL conical tubes (Genesee, San Diego, CA). The microbeads were washed twice with 100% ethanol and pelleted by 5-minute centrifugation at 400 g. The microbeads were rehydrated overnight with 45 mL of PBS on a shaker. After rehydration, the microbeads were consecutively passed through 100, 70, and finally 40 μm cell strainers (Thermo Fisher Sci.), increasing the monodispersity of the bead populations to more closely mimic the distribution of cell populations through the removal of large beads and aggregates. Proper polymerization of PAAm microbeads was confirmed by FT-IR (FIG. 5).

Example 16: Microbead FT-IR Analysis

The structure of the microbeads was assessed using Fourier transform infrared spectroscopy (FT-IR) with attenuated total reflectance (ATR) using a Nicolet iS50 FT-IR (Thermo Fisher Scientific, Madison, WI, USA). Prior to scanning, the polyacrylamide (PAAm) microbeads were concentrated with centrifugation and lyophilized with a VirTis Benchtop 4K lyophilizer (SP Scientific, Gardiner, NY) for 48 hours to produce condensed dry pellets. The observed spectrum of the fingerprint region (FIG. 5) demonstrated absorbance peaks at the expected wavenumbers for polymerized PAAm, corresponding to the flexural stretching of —NH bonds of both amide I and II (about 1613 cm-1), the C—N groups of both amides (about 1441, 1351, and 1281 cm-1), and the tensional stretching of the C=O groups of amide I (about 1675 cm-1) (Ghorbaniazar, P. et al. *Adv. Pharm. Bull.,* 2015, 5(2), 269-275).

Example 17: Characterization of Elastic Properties of Microbeads

The elastic properties of individual microbeads were characterized through indentation testing with an MFP-3D-Bio atomic force microscope (AFM, Asylum Research, Santa Barbara, CA) equipped with a spherically tipped cantilever, made by adhering a 5 μm diameter, polystyrene bead (Microbeads AS, Skedsmoorset, Norway) to a tip-less, silicon nitride cantilever (Bruker Corporation, MLCT10, k~0.03 N/m), using an approach velocity of 10 μm/s, and a trigger force of 5 nN (about 1-2 μm indentation). The elastic/Young's moduli (Eelastic) of the microbeads were determined from force vs. indentation curves using a modified Hertz model, as described previously in Dimitriadis, E. K. et al. *Biophysical Journal,* 2002, 82, 2798-2810.

Figure 3:
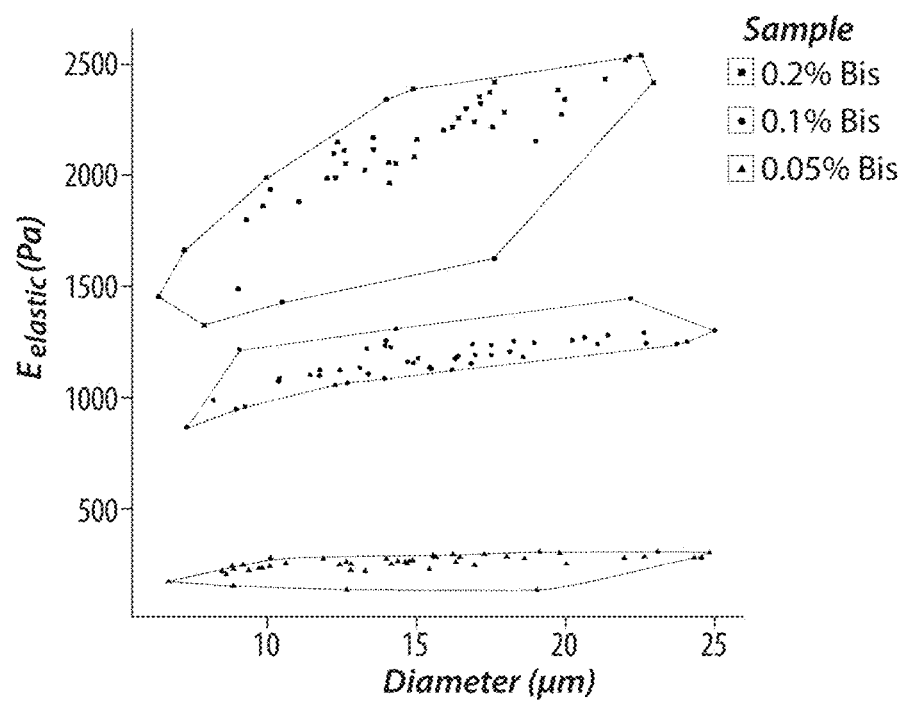
FIG. 3 is a scatter plot that demonstrates the ranges of sizes and elastic moduli for each polyacrylamide formulation (PAAm). The microbead elasticity and size distributions were measured by atomic force microscopy. The bottom shaded region represents the most compliant 0.05% PAAm formulation (250±10 Pa, 14±5 min), the middle shaded region represents 0.1% PAAm formulation (1200±100 Pa, 15±4 µm), and the top shaded represents 0.2% PAAm formulation (2100±300 Pa, 14±4 µm).
Figure 4:
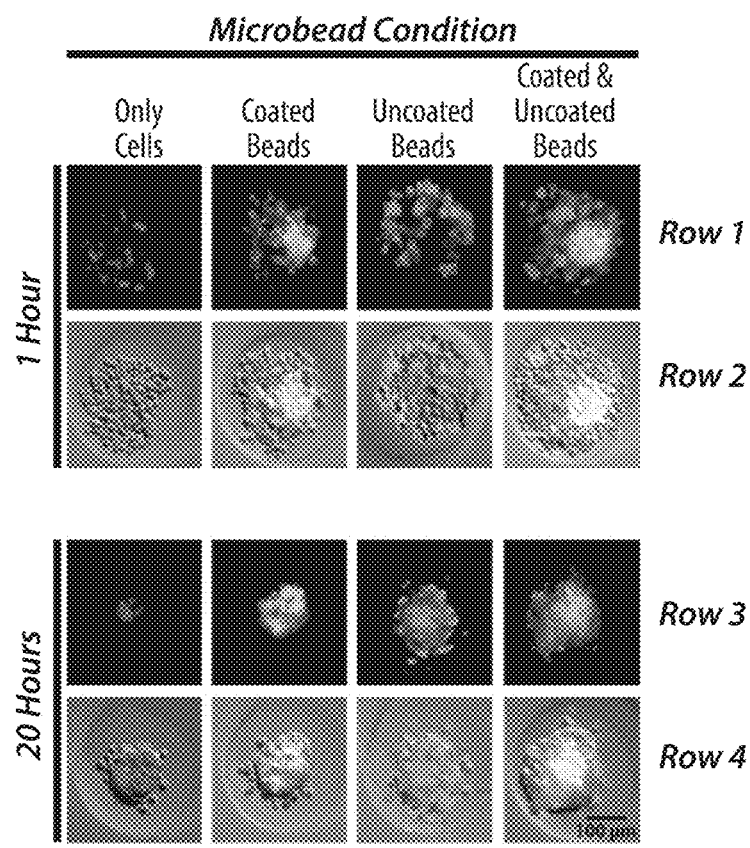
FIG. 4 is a set of fluorescence and phase contrast microphotographs demonstrating that dyes can be used for cells and binding of cells by protein-coated microbeads. The fluorescence and phase contrast microphotographs demonstrate the binding of MG-63 osteosarcoma cells stained with calcein AM (blue, 10 µg/mL, AnaSpec Inc. Fremont, CA) to collagen-coated (green, pyrene-based dye, Sharpie) and uncoated (red, rhodamine-based dye, Sharpie) microbeads. The images in rows 1 and 2 were obtained 1 hour post seeding and the images in rows 3 and 4 were obtained 20 hours post seeding. Rows 1 and 3 are fluorescence microphotographs and rows 2 and 4 are phase contrast microphotographs with superimposed fluorescence images. The spheroids containing cells alone (left column) assembled into compact structures over 20 hours. Spheroids containing cells and coated microbeads (center-left column), cells and uncoated microbeads (center-right column), or cells and both coated and uncoated microbeads (right column) formed similar compact spheroids having different levels of incorporation of the microbeads by binding to the cells of each of the two types of microbeads.
Figure 6:
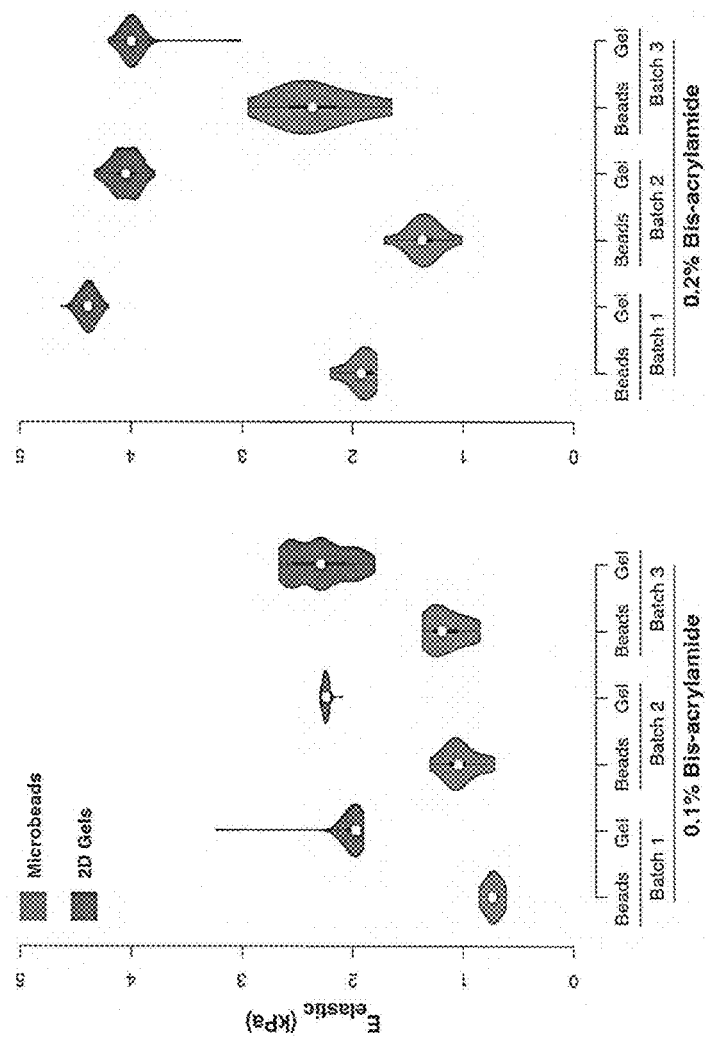
FIG. 6 is a set of violin plots that demonstrate batch-to-batch similarity and extent of variation in elasticity of PAAm gels and microbeads. The violin plots display the elastic moduli distributions of three batches of microbeads (bottom three shapes in each plot) and paired thin gels (top three shapes in each plot) generated with 4% acrylamide and either 0.1 or 0.2% bis-acrylamide, measured using an atomic force microscope (AFM). The circles inside the shaded areas represent medians, thick black lines represent 25-75% quartiles, and thin black lines represent the range of data set in which the outliers have been removed. The elastic modulus for a given microbead batch was typically observed to have a standard deviation of less than 15% of the mean and consistent size distributions. Successive batches of microbeads created using the same formulation did not always yield the same average elastic modulus (Table 2) although the size distributions after 40 μm filtering remained in good agreement. The methods herein include mechanically sampling individual microbead batches to determine that the properties appropriate for a given application.

As has been demonstrated in two-dimensional gels, (Engler, A. J. et al. *Cell,* 2006, 126, 677-689) the elastic modulus observed herein of PAAm hydrogel microbeads was positively correlated to the concentration of the bis-acrylamide cross-linker, which connects linear chains of acrylamide together. Thus, mechanically distinct microbead populations were generated by changing only the volume and amounts of bis-acrylamide in the polymer solution (FIG. 3). Microbead moduli of the microbeads were observed to be approximately half that of 2D gels using the same PAAm formulation (FIG. 6). This phenomenon is likely due to the surfactant adsorbing instead of acrylamide sub-units as well as interacting with looped regions of the polymer chains, altering the amorphous structure of the polymer and resulting in reduced mechanical stability (Kronberg, B. et al. *Surface Chemistry of Surfactants and Polymers,* John Wiley & Sons, Hoboken NJ, 2014). The elastic modulus for a given microbead batch was observed to be a standard deviation of less than 15% of the mean and consistent size distributions. While successive batches of microbeads created using the same formulation did not always yield the same average elastic modulus (Table 2 and FIG. 6), size distributions after 40 μm filtering were observed in good agreement. Individual microbead batches were accordingly mechanically characterized to confirm properties that align with those needed for a given application.

TABLE 2

Batch-to-batch variation in microbead size and compliance

|  | Batch # | 0.1% bis-acrylamide | 0.2% bis-acrylamide |
|---|---|---|---|
| Diameter: | 1 | 28 ± 7 µm | 27 ± 8 µm |
| Microbeads | 2 | 29 ± 8 µm | 29 ± 7 µm |
|  | 3 | 30 ± 9 µm | 27 ± 8 µm |
| $E_{elastic}$: | 1 | 720 ± 70 Pa | 1920 ± 120 Pa |
| Microbeads | 2 | 1010 ± 150 Pa | 1340 ± 150 Pa |
|  | 3 | 1140 ± 160 Pa | 2300 ± 350 Pa |
| $E_{elastic}$: | 1 | 2010 ± 170 Pa | 4390 ± 70 Pa |
| Gel | 2 | 2240 ± 30 Pa | 4050 ± 120 Pa |
|  | 3 | 2270 ± 250 Pa | 3970 ± 150 Pa |

Example 18: PAAm Variability in Diameter and Elastic Modulus

Three sets of microbead populations were generated for two different PAAm formulations to examine variability in diameter and elastic modulus (Table 2). Microbead batches were generated using either 0.2% or 0.1% bis-acrylamide formulations with a 1500 RPM stir rate, followed by serial filtration through 100, 70, and 40 µm cell strainers.

No significant differences were observed in the size distributions across batches (p more than 0.4) or formulations (p more than 0.3; Table 2). In general, 0.2% bis-acrylamide microbeads reliably exhibited higher elastic moduli than 0.1% bis-acrylamide microbeads; however, batch-to-batch variation in elastic moduli was significant (p less than 0.04; FIG. 6). Due to this observation, combining multiple batches of the same formulation into a single population is contra-indicated, since this would result in a population with a multi-modal distribution. For applications requiring microbeads of a specific elasticity, sufficient microbeads were prepared in a single batch, which was mechanically characterized to confirm the desired properties.

Paired 2D gels were generated using a 75 µL sample of the PAAm solutions from each of the PAAm solutions by sandwiching the droplet between two coverslips. Once polymerized (about 15 minutes at room temperature), the gels were rehydrated in deionized water for 30 minutes and one of the coverslips was subsequently removed with forceps. The gels were washed three times with PBS and equilibrated for at least one hour before characterizing their elastic moduli with AFM. For AFM single indentation experiments, the same cantilever and indentation settings used for microbead characterization were used for the thin gels. Average elasticities were calculated from three sets of sixteen indentations (n=48) spread equally over 90×90 µm regions (Table 2).

Example 19: Fluorescent Staining of Microbeads

Figure 7:
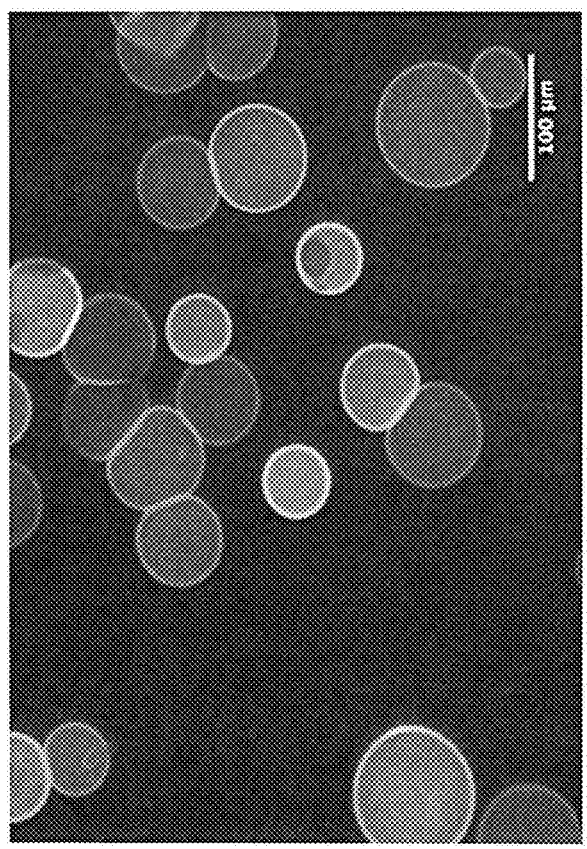
FIG. 7 is a microphotograph of a mixture of microbeads stained with each of three fluorescent dyes useful for visualization. Separate batches of microbeads were stained with each of three different fluorescent dyes to create distinct visual tags that are useful to track microbead location. Teal colored beads were obtained by staining with pyrene dye, pink colored beads were obtained by staining with a mix of pyrene and triphenylmethane dyes, and red colored beads were obtained by staining with rhodamine. Each of these colors were observed in the mixture.

Microbeads, following polymerization, were stained fluorescently with pyrene, rhodamine, or triphenylmethane dye(s) (Sharpie, Oak Brook, IL, Table 3 & FIG. 7). A suspension of 10 million microbeads/mL in deionized water was spiked with 20 µL/mL of dye (dilution factor 1:50), vortexed, and further diluted 1:1 with 100% ethanol. The suspension was then centrifuged for five minutes at 400 g, supernatant removed, and pellet resuspended in 15 mL of deionized water. Following this wash, the suspension was centrifuged for five minutes at 1000 g with the brake disabled to reduce resuspension of the microbead pellet during rapid deceleration. Subsequent centrifugations followed this procedure. The pellet was resuspended in PBS at the desired final concentration for the intended application. The dye likely to binds to the PAAm via hydrogen bonding between the carboxylic groups of the dye and the amide of the acrylamide sub-units. Although dye can likely be incorporated directly into the PAAm solution, the option to stain after fabrication allows a single microbead batch to be conveniently used in aliquots, each with one or more of multiple dyes. The addition of fluorescence is also useful for determining bead sizes, tracking their movement in culture systems, or for distinguishing different microbead formulations.

Example 20: Fluorescent Stains

Fully polymerized microbeads were stained with a variety of fluorescent dyes extracted from Sharpie Liquid highlighters (summarized in Table 3) and imaged using a Nikon Eclipse Ti-U epifluorescent microscope (Nikon Instruments, Melville, NY) equipped with a QICAM 12-bit digital camera (QImaging, Surrey, BC, Canada; FIG. 7).

TABLE 3

Fluorescent highlighter dyes and their respective excitation/emission wavelengths

| Highlighter color | Dye contained | Excitation | Emission |
|---|---|---|---|
| Yellow | Pyrene | 330-490 nm | 440-545 nm |
| Pink | Rhodamine | 530-560 nm | 595-650 nm |
| Green | Pyrene/ Triphenylmethane | 590-645 nm | 665-730 nm |

The fluorescence spectra of these dyes are partially dependent on pH. As such, the wavelength range of the filter cubes used to image each dye is reported. The green dye, which includes pyrene dye, exhibits dim fluorescence in the same channels as the yellow dye but with the addition of bright signal at longer wavelengths.

Example 21: Microbead Size Characterization

Microbead size distributions were determined through the analysis of epifluorescent images, using ImageJ. Sixteen images of pyrene-stained microbeads were acquired using a Cytation3 Cell Imaging Multi-Mode Reader (Biotek Instruments Inc., Winooski, VT) using a 10× objective. Since fluorescence intensity was not quantified for this example, imaging parameters were optimized for each population using the auto focus and auto exposure features available through the provided software (Gen 5, version 2.05.5, Biotek). Images were loaded into Image J (version 1.47, National Institute of Health, Bethesda, MD) and converted to binary images through the application of an intensity threshold. The additional binary functions, "fill holes" and "watershed," were applied to account for lessened fluorescence intensity in the central region of microbeads and identify edges of microbeads contacting each other, respectively. The area of the particles was then assessed with the "analyze particles" feature with additional thresholding to remove the detected regions of high intensity that were less than 5 pixels$^2$ in area or less than 0.60 in circularity. Recorded areas that correspond to out of focus microbeads were removed manually on a per image basis. The measured areas were then converted from pixels$^2$ to µm$^2$ using the appropriate pixel ratio associated with the imaging system. The effective diameters (in µm) were then calculated from the area measurements.

Example 22: Microbead Loss During Processing

A significant percentage of the microbead populations was lost throughout the various washes and treatment stages included in the described protocol, particularly after coating with protein. Microbeads were counted with a hemocytometer to track the loss of beads from the sulfo-SANPAH and collagen-coating treatment steps, identified as the primary points of concern. As summarized in Table 4, a loss of nearly 80% was observed for one test case, representative of typical runs. Losses of these magnitudes should be anticipated and compensated by initial choice of starting material masses, particularly for any application that incorporates protein coatings as a feature of the microbead.

TABLE 4

Microbead yield following high-loss, processing steps

| Formulation | % of Original (after Sulfo-SANPAH) | % of Original (after Collagen coating) |
|---|---|---|
| 0.05% bis-acrylamide | 68% | 42% |
| 0.1% bis-acrylamide | >99% | 29% |
| 0.2% bis-acrylamide | 95% | 21% |

Example 23: Cell Adhesion

To make the microbead surfaces recognizable for cell adhesion, Sulfo-SANPAH (CovaChem, LLC., Loves Park, IL) was used to conjugate rat tail collagen type-I (Millipore) to the PAAm bead surface. This reaction proceeds by covalently linking the UV-sensitive nitrophenylazide group of the sulfo-SANPAH to the PAAm surface after exposure to a UV light source. The collagen then binds to the free N-hydroxysuccinimide ester to create a recognizable surface for cells to interact with (Tse, J. R. et al. *Current Protocols in Cell Biology*, 2010, Unit 10.16, 1-16). After the microbeads were washed and stained, they were centrifuged and resuspended in 500 μL of 1 mg/mL Sulfo-SANPAH solution. The tube was uncapped and exposed to ultraviolet light in a Rayonet UV reaction chamber (The Southern New England Ultraviolet Co., Branford, CT) for 15 minutes. Samples were then flooded with 14.5 mL of deionized water, and were centrifuged and subjected to a second Sulfo-SANPAH treatment.

After re-pelleting, the microbeads were resuspended in 5 mL of deionized water and transferred to a polyethylene terephthalate (PET) tube (Corning Inc., Corning, NY), which was observed to exhibit reduced microbead adhesion compared to other plastic alternatives. Collagen type-I was added to the suspension to yield a final concentration of 100 μg/mL, greater than 1000-fold molar excess to accessible amide groups of the microbeads. The suspension was vortexed and placed on a shaker overnight at 4° C. The next day, 50 μL of 1 M HCl was added to the suspension to create a slightly acidic environment (pH ~6.9), intended to prevent collagen gelation that can aggregate and entrap microbeads. After five minutes, 10 mL of deionized water was added to the tube followed by centrifugation and a second wash in 15 mL deionized water spiked with 50 μL of 1 M HCl. The microbead pellet was then resuspended in PBS to yield the desired final concentration. Significant loss of microbeads can occur during treatment and wash steps (30-80%, Table 4), primarily due to cell aggregation and adhesion to plastic after being coated with collagen. To investigate how cells interacted with the compliant PAAm microbeads, MG-63, osteosarcoma cells (ATCC, Manassas, VA) were seeded into 2% agarose 3D Petri Dishes® (#24-96-Small, Microtissues, Inc., Providence, RI) either alone, with only uncoated or collagen-coated microbeads, or with both uncoated and collagen-coated microbeads ($E_{elastic}$ about 1 kPa) at a 4:1 ratio (cells:microbeads, 100,000 particles/well). Results showed that cells incorporated collagen-coated microbeads into self-assembled spheroids, confirming cell recognition.

Cells were observed in examples herein to have interacted differently with uncoated microbeads, which lacked a complementary ligand, either excluding them from the spheroid or randomly entrapping them in a dispersed manner. The demonstrated ability to functionalize the microbeads for cellular recognition makes them a promising component for 3D scaffolding technologies. While PAAm, as a material, is non-ideal for tissue engineering applications because it is non-biodegradable, there are biocompatible polymer alternatives that may be compatible with the presented methodology. For investigations purely into the effects of a passive mechanical signal on cell behavior, a stable polymer such as PAAm is ideal since a biodegradable polymer would likely undergo drastic changes in mechanical properties.

Example 24: ASC, Microbead, and Gel Characterization

Figure 8:
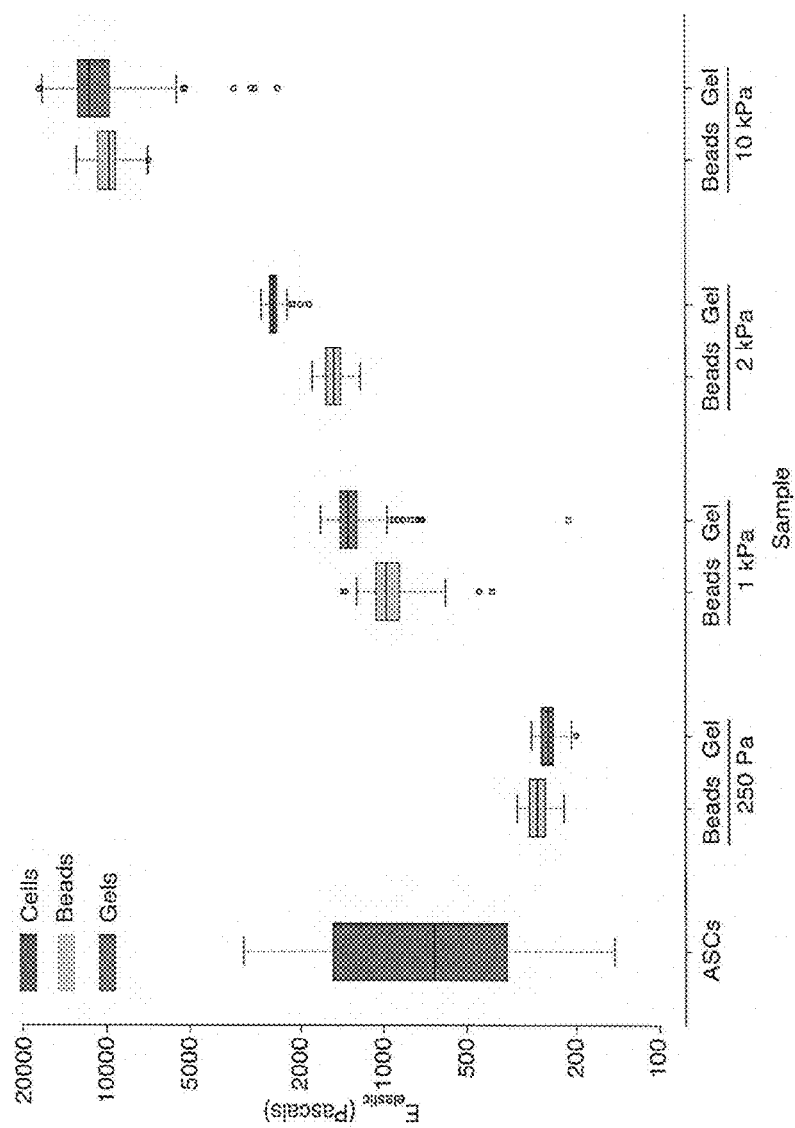
FIG. 8 is a set of box and whisker plots that show data obtained for elastic modulus distributions of adipose-derived stem cells (ASCs), microbeads, and thin gels. The three most compliant microbead populations were observed to be within the range of the ASC population. The formulation depicted on the right is an order of magnitude stiffer than the cells. The ASC population was observed to exhibit the most heterogeneity in elasticity, such that the elastic moduli of three most compliant microbead populations were within the wide range exhibited by the cells, ideally mimicking sub-populations within the stem cell population.
Figure 9:
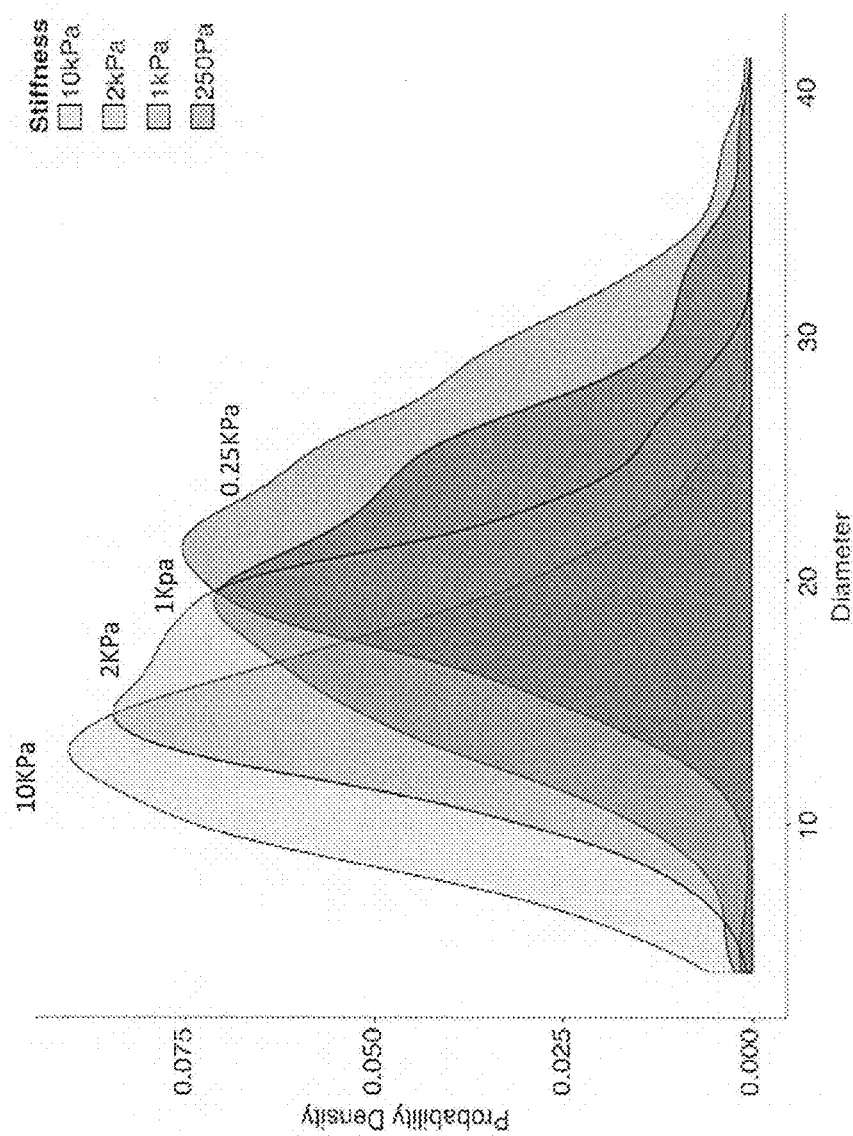
FIG. 9 is a density plot of collagen coated microbead diameter distributions for each polyacrylamide formulation: 0.25 kPa, 1 kPa, 2 kPa, and 10 kPa. The size distributions of each of these formulations encompass the typical size of mammalian cells (5-50 μm).

The elastic moduli of human ASCs and PAAm microbeads and their paired gels were assessed with AFM (FIG. 8). Each microbead population and paired gel was observed to be mechanically distinct from the other formulations (p less than $1*10^{31}$). The ASC population was observed to exhibit the most heterogeneity in elasticity, such that the elastic moduli of the three most compliant microbead populations were observed to be within the wide range exhibited by the cells, ideally mimicking sub-populations within the stem cell population. Additionally, the stiffest gels and microbeads were observed to be approximately an order of magnitude higher in elasticity than the average ASC. Variability in the average diameter of microparticles produced with each formulation of the different preparations of microbeads was also observed to be within the typical size range of mammalian somatic cells (FIG. 9).

Example 25: Changes in Spheroid Mechanophenotype

Figure 10A:
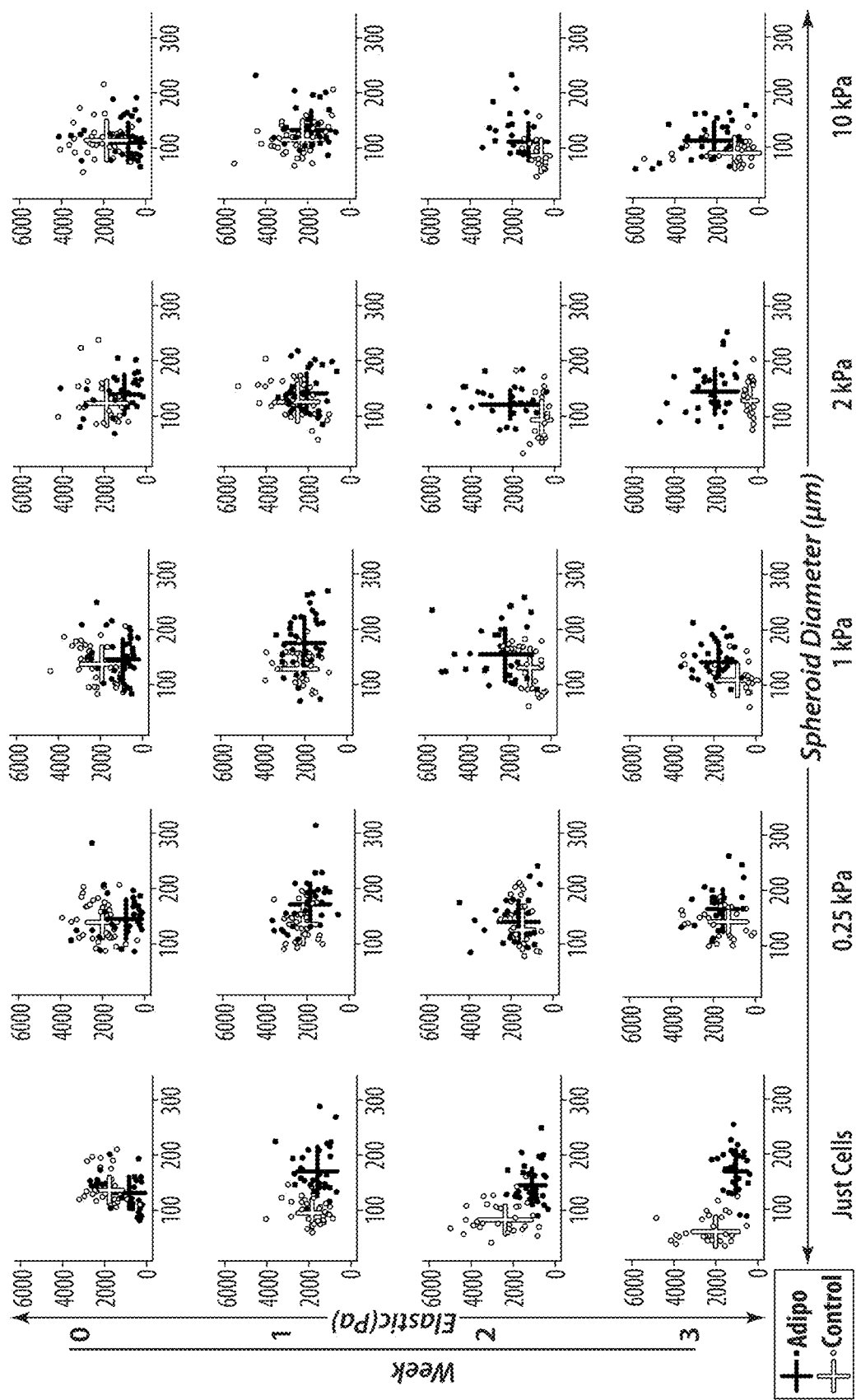
FIG. 10A and FIG. 10B are sets of scatter plots and microphotographs, respectively, showing temporal changes in composite spheroid elasticities and diameters.
Figure 10B:
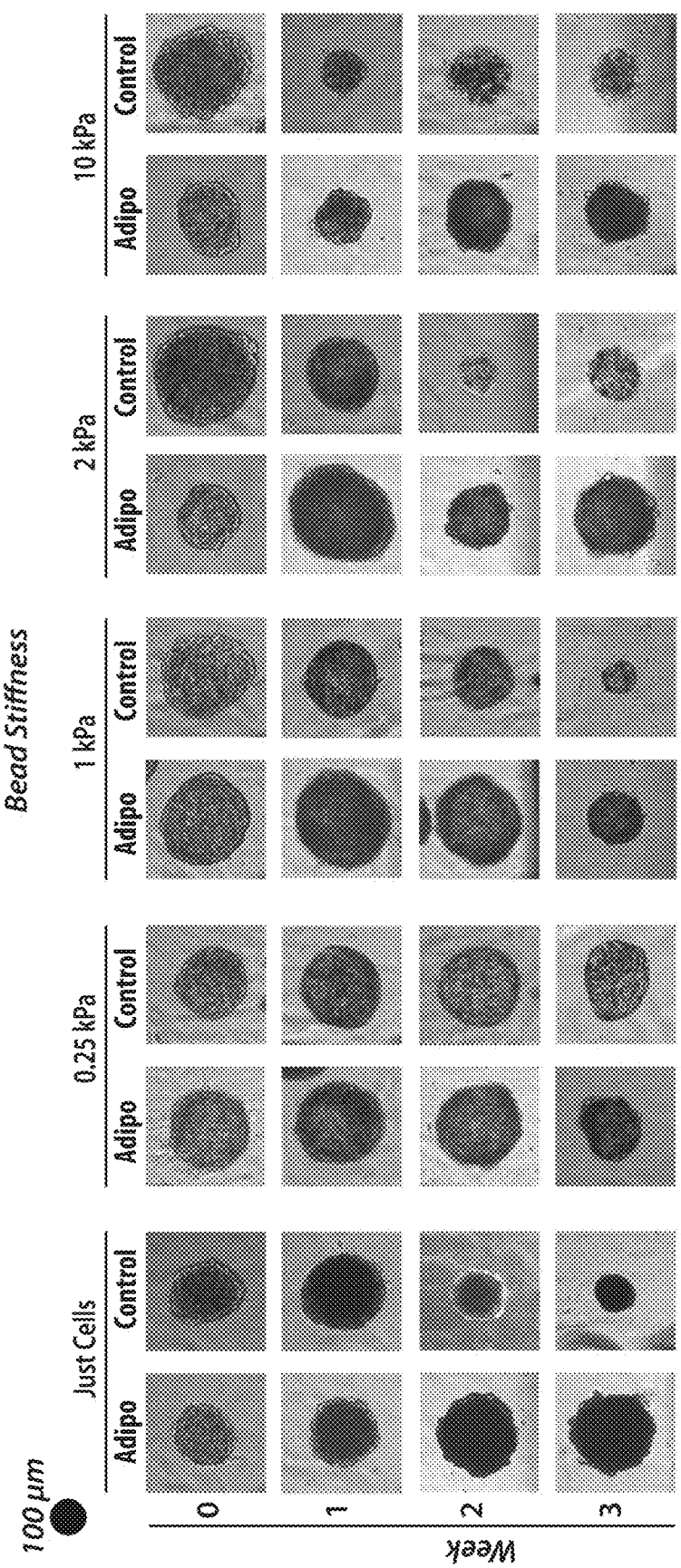

Cell-only and composite spheroids cultured in adipogenic medium were observed to quickly respond to the adipogenic chemical factors, signified by the lower average elastic moduli of the adipogenic spheroids (840±930 Pa) compared to control spheroids (1910±830 Pa) within the first 48 hours of exposure to adipogenic induction medium, independent of mechanical cues (p less than $9*10^{-18}$, FIG. 10). After a week in culture all adipogenic spheroids were observed to exhibit an increase in elastic moduli (1800±760, p less than 0.004), and control samples were observed to remain unchanged (2160±890, p more than 0.1). Comparing effects of chemical cues on the elasticities of paired microbead conditions, adipogenic spheroids were observed to be significantly more compliant than paired controls (p less than 0.03) after 48 hours of culture. However, these differences were nullified by the increased elasticity of adipogenic spheroids after a week in culture (p more than 0.2), after which only 0.25 kPa spheroids still exhibited significantly lower elastic moduli in adipogenic medium compared to stromal medium (p less than 0.01). Cell-only spheroids in adipogenic medium also were observed to have stiffened during the first week in culture, and then to have exhibited more compliant mechanophenotypes after two weeks.

After 21 days in culture, spheroids incubated under most of the microbead conditions, except 0.25 kPa, were observed to exhibit significant differences in elastic moduli in comparing paired adipogenic and control samples (p less than 0.003). By the end of the induction period, cell-only spheroids in adipogenic medium (1030±410 Pa) were observed to be significantly more compliant than those in control medium (2010±1030 Pa, p less than $6*10^{-6}$). Adipogenic 1 kPa, 2 kPa, and 10 kPa composite spheroids all exhibited increased in elasticity compared to spheroids in control media (p less than 0.0003).

There were also significant differences in the elastic moduli in the various microbead conditions after 21 days in culture. Adipogenic spheroids cultured without microbeads were observed to be significantly more compliant than any of the composite spheroids cultured in presence of these chemical induction factors. Additionally, 0.25 kPa composite spheroids were observed to be significantly more compliant (1570±700 Pa) than the 10 kPa samples in adipogenic induction medium (2000±1320 Pa, p<0.03). Though average composite spheroid elasticity was positively correlated with the stiffness of incorporated microbeads (cross-correlation coefficient=0.71), no other adipogenic composite spheroids were observed to exhibit significantly different elastic moduli from one another (p more than 0.05). After 21 days of culture in control medium, spheroids without microbeads were observed to be significantly stiffer than composite spheroids containing microbeads with elastic moduli of 1 kPa or greater (p less than 0.004), but not 0.25 kPa microbeads (p more than 0.1). Additionally, 0.25 kPa composite spheroids were observed to have significantly higher elastic moduli (1230±940 Pa) than 2 kPa (330±130 Pa) and 10 kPa control samples (950±1310 Pa, p<0.02), but not 1 kPa composite spheroids (770±1030 Pa, p >0.08). Further, 1 kPa composite spheroids were observed to be stiffer than those with 2 kPa microbeads (p less than 0.005) but not 10 kPa samples (p more than 0.2).

In summary, spheroids containing only cells increased in elastic modulus as a function of time after culture in control medium, and became more compliant after culture in adipogenic medium. Composite spheroids exhibited increases in elastic moduli that correlated with the stiffness of incorporated microbeads for adipogenic samples. Control samples containing stiffer microbeads exhibited a decrease in spheroid stiffness, attributed to spheroid dissociation.

Example 26: Change in Spheroid Diameters

Initially, cell-only spheroids and composite spheroids incorporating 0.25, 1, and 10 kPa microbeads were observed to exhibit no differences in diameters across media conditions (p more than 0.08). Composite 2 kPa spheroids were observed to attain slightly larger diameter in adipogenic medium compared to control samples (p less than 0.02).

Spheroids cultured without microbeads in control medium were observed to contract, and were significantly smaller than those cultured in adipogenic medium after just one week in culture (p less than 0.02). Control cell-only spheroids continued to contract throughout the 21-day culture period, such that spheroids from each time point were significantly smaller than samples from the previous time point (p less than 0.03). Cell-only spheroids in adipogenic medium increased in size over the 21-day induction period (p less than 0.00008).

There were no significant changes observed in the diameters of 0.25 kPa composite spheroids after 21 days in culture, independent of media environment (p more than 0.06). Composite spheroids containing 1 kPa microbeads were observed to decrease in spheroid diameter after 21 days in control media (p less than 0.04). No changes were observed in adipogenic media compared to controls (p more than 0.6). Composite spheroids containing 2 kPa microbeads did not exhibit temporal changes in diameter in either media condition (p more than 0.1) as a function of time. Composite 10 kPa spheroids decreased in spheroid size at 14 days of culture in control medium (p less than 0.0002), and there was no change was observed in paired adipogenic spheroids after 21 days (p more than 0.5).

With respect to microbead stiffnesses, 10 kPa composite spheroids in adipogenic medium initially had slightly smaller diameters compared to the other conditions (p less than 0.03). For control samples, 0.25 and 1 kPa composite spheroids were initially significantly larger than 10 kPa spheroids (p less than 0.02), and cell-only spheroids were larger than both 2 and 10 kPa composite spheroids (p less than 0.02). After 21 days in culture, cell-only spheroids were observed to be significantly smaller than under other microbead conditions within control samples (p less than 0.00002). The 0.25 kPa microbead control samples were observed to be significantly larger than the other control spheroids (p less than 0.03), excluding 2 kPa composite spheroids (p more than 0.2). The control media 10 kPa samples were observed to be significantly smaller than 1 kPa spheroids at 21 days in control medium (p less than 0.03). For adipogenic samples, cell-only spheroids were observed to be significantly larger than 1, 2, and 10 kPa composite spheroids after 21 days in culture (p less than 0.02). The 10 kPa adipogenic samples were significantly smaller than other adipogenic spheroids (p less than 0.02) with the exception of those containing 1 kPa microbeads (p more then 0.05). The 0.25 kPa composite spheroids were also significantly larger than the 1 kPa composite spheroids (p less than 0.04).

Example 27: Two-Dimensional ASC Morphology Imaging

Figure 11:
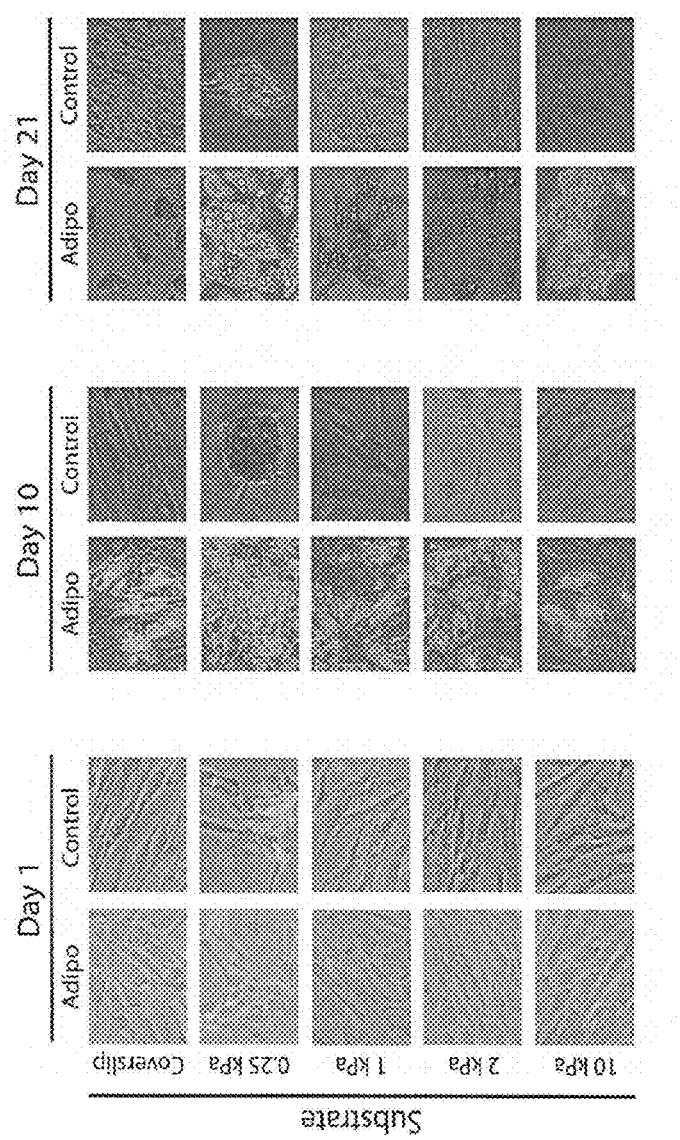
FIG. 11 is a set of microphotographs of ASCs after 1, 10, and 21 days (left to right) in culture in either adipogenic (left) medium or control (right) medium on coverslips or 0.25, 1, 2, or 10 kPa PAAm gels (top to bottom). Adipogenic medium consisted of control medium supplemented with 0.5 μM 3-isobutyl-1-methylxanthine, 10 μM insulin, 200 μM indomethacin, and 1 μM dexamethasone and Control medium consisted of DMEM/F-12 supplemented with 10% FBS, and 1% antibiotic/antimycotic. ASCs were observed to produce visible lipids after 10 days in culture with the most dramatic production on the most compliant gel. After 21 days in culture, lipid droplets were observed to have increased in diameter and lipid droplet size independent of substrate.

Upon initial seeding onto coverslips and two-dimensional thin gels, ASCs were observed to exhibit similar morphologies independent of substrate stiffnesses (FIG. 11). ASCs cultured on 2D 0.25 kPa gels were observed to be slightly less spread than the other substrate conditions after 24 hours of culture in either media environment. After ten days in culture, ASCs cultured with soluble adipogenic induction factors had initiated lipid synthesis under each substrate conditions, with the most robust lipid production in the 0.25 kPa samples. Control samples did not exhibit noticeable lipids after ten days in culture; however, cells cultured on 0.25 kPa gels appeared to form spheroids/nodules in control medium without induction factors. After 21 days in culture, the amount of the lipids produced in adipogenic media was observed to have increased in each substrate stiffness and it was little difference between conditions. Though not quantified, adipogenic samples on coverslips were observed to have slightly attenuated lipid production compared to those grown on gels. In control medium, ASCs in 0.25 kPa gels were observed to form spheroids/nodules, producing some small amounts of lipids. A small amount of lipids was observed in the 1 kPa control samples after 21 days in culture. The ASCs in other control conditions of gel were observed to exhibit similar spread morphologies without visible lipid production.

Example 28: Lineage-Specific Gene Expression

The expression of mRNA corresponding to the adipogenic genes, PPARG and FABP4, was assessed relative to the reference gene, GAPDH, using qPCR for each of the samples cultured in adipogenic or control medium in 2D and 3D, with each of the PAAM described herein.

Figure 12:
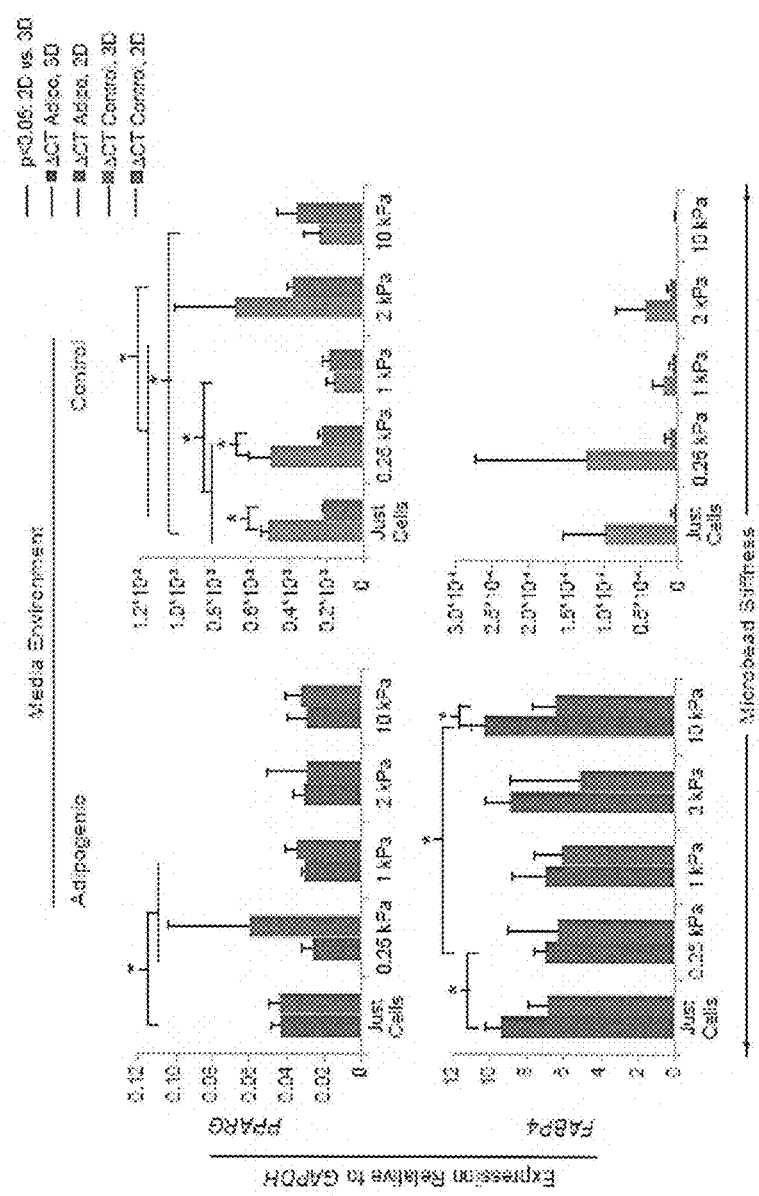
FIG. 12 is a set of bar graphs showing adipogenic gene expression of ASCs after 21 days of exposure to various mechanical cues in 2D and 3D in presence of chemical induction factors and control absent factors. The expression was observed of PPARG (top) and FABP4 (bottom) of ASCs grown in adipogenic (left) and control (right) media. Significance bars represent student's t-test p-values<0.05 between 2D and 3D culture systems, 3D adipogenic samples, 2D adipogenic samples, 3D control samples, and 2D control samples.

Culturing ASC 3D spheroids to soluble adipogenic induction factors was observed to have resulted in significant upregulation in the expression of both PPARG and FABP4, compared to paired controls absent the factors (p less than 0.02, FIG. 12). However, for 2D cultures, no significant differences were observed in the expression of PPARG for 0.25 and 2 kPa for cells on gel substrates. Further no differences were observed in the expression of FABP4 only for 2 kPa gels (p more than 0.1).

Statistically significant differences were observed in expression of PPARG between 2D and 3D samples for cell-only and 0.25 kPa control samples (p less than 0.03), and were observed for expression of FABP4 for adipogenic samples with 10 kPa microbeads (p less than 0.03). Cell-only and 0.25 kPa spheroids exposed to control media were observed to exhibit a significant increase in the expression of PPARG compared to spheroids with 1 kPa microbeads incorporated (p less than 0.02). A significant upregulation of PPARG was observed in ASCs cultured on 2 kPa thin gels in control medium compared to those grown on 0.25 or 1 kPa gels or coverslips (p less than 0.003).

Example 29: Spheroid Formation Timelapse

Figure 13:
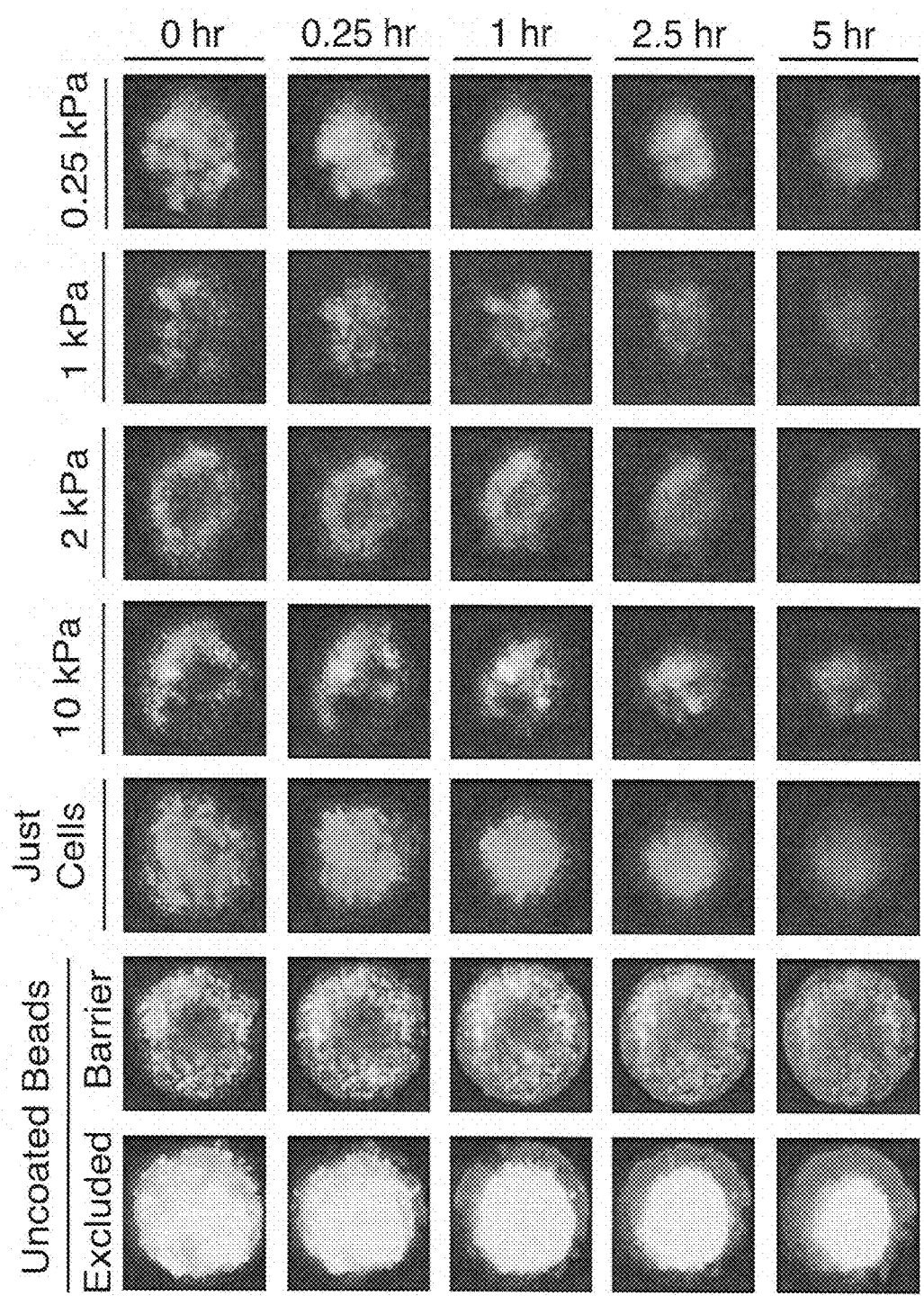
FIG. 13 is a set of microphotographs showing initial (five hour) composite spheroid formation. Human ASCs were observed to bind coated microbeads with varying elastic moduli (0.25 kPa, 1 kPa, 2 kPa, 10 kPa, red) and form a composite spheroid. Cells did not bind uncoated 1 kPa microbeads, and formed either small aggregates (labeled "Barrier") or formed cell only spheroids absent uncoated microbeads (labeled "Excluded"). Microwells containing double the number of ASCs and no microbeads formed spheroids roughly the same size as the composite spheroids. Increasing time of incubation is labeled from 0 hrs, which was approximately 15-20 minutes after the cells and beads or control are seeded.

Cells incorporated collagen type-I coated microbeads into self-assembled spheroids (FIG. 13). Cells appeared to first bind to microbeads, forming small aggregates, subsequently coalescing into a composite spheroid. Throughout the five-hour timelapse, cell-only spheroids appeared similar in size to composite spheroids containing coated beads. Uncoated microbeads interacted differently with cells and were observed either to be largely excluded from the spheroids, or to act as a barrier or inhibitor to aggregation as cells were observed to form smaller aggregates that did not condense into a spheroid.

Example 30: Confocal Imaging

Figure 14:
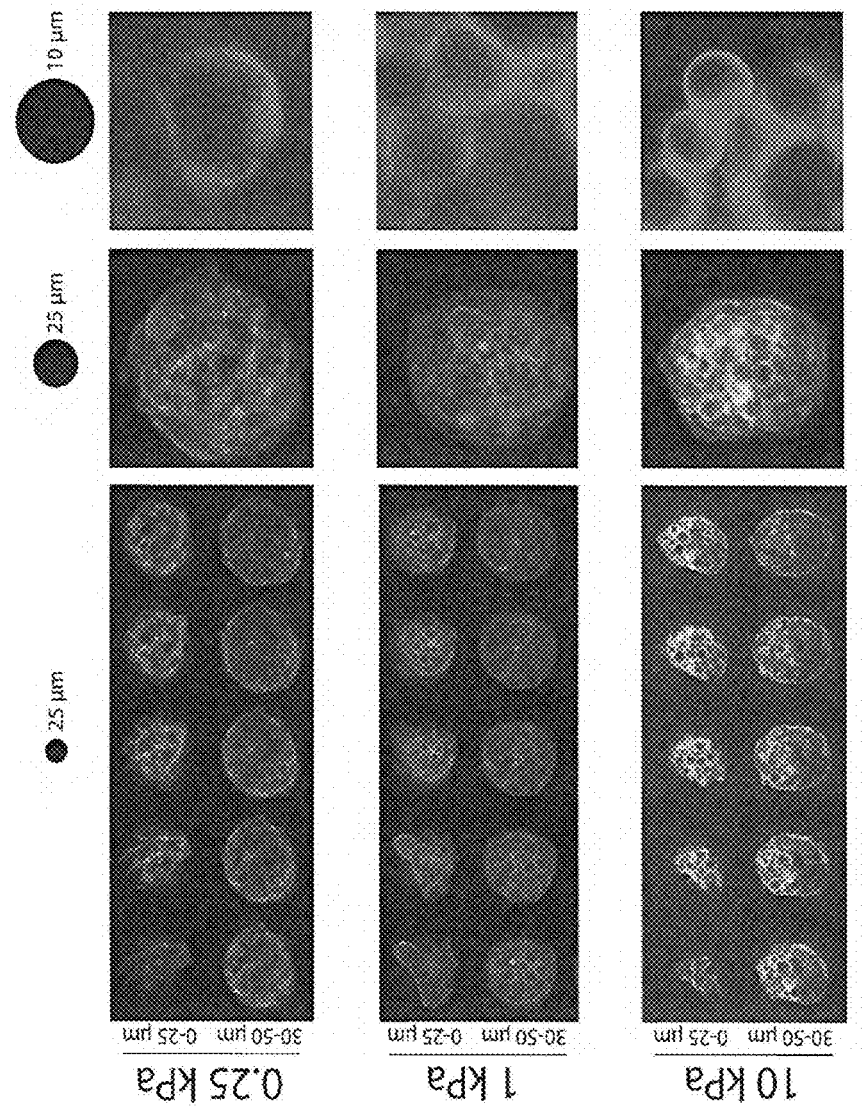
FIG. 14 is a set of microphotographs of composite spheroids and microbeads showing deformation of these structures as a function of time of the adipogenic composite spheroids containing 0.25, 1, and 10 kPa microbeads after 21 days in culture. The nuclei of cells were stained with DAPI, the actin cytoskeletal structures were stained with phalloidin, and the microbeads were stained with rhodamine. The left set shows representative z-stacks of the first 50 μm of the z-stacks in 5 μm steps, the center set represents a 3D projection of the z stacks, and the right set illustrates an isolated region of microbeads to demonstrate differences in the deformation. Scale circles represent 25, 25, and 10 μm diameters from left to right, respectively.

Confocal imaging demonstrated that microbeads were largely sequestered to the center of composite spheroids after 21 days in adipogenic medium, independent of microbead elasticity (FIG. 14). Very few cells, or cell extensions, were seen between microbeads throughout the z-stacks of the spheroids. Spheroids containing 10 kPa microbeads exhibited increased actin cytoskeletal staining compared to those with 0.25 or 1 kPa microbeads. Additionally, the more compliant 0.25 and 1 kPa microbeads were observed to be noticeably deformed due to the contractile forces of the surrounding cells, and 10 kPa microbeads maintained their spherical shapes.

Example 31: Cryopreservation of Cells

The cell culture is inspected for contamination from bacteria, fungi, *Mycoplasma*, and viruses immediately before cryopreservation and contaminated cultures are discarded. A freeze medium consisting of complete growth medium and 5% DMSO (ATCC catalog no. 4-X) is prepared. The cells are collected by gentle centrifugation (10 min at 125×g) and resuspended in the freeze medium. A suspension containing hyper compliant polymer particles or PAAm microbeads is prepared. The cell suspension and the microparticle suspension are mixed such that the total concentration of the cells and the microparticles is at least about $1\times10^6$ to at least about $5\times10^6$ of the combination of cells and microparticles/ml. In some embodiments, dimethyl sulfoxide (DMSO) is added either to the cell suspension and/or to the microparticle suspension.

The vials are labeled with the name of the cell line and the date. About 1 ml to about 1.8 ml of the cell and microparticle suspension is aliquoted in to each of the vials and the vials are sealed. The cell and the microparticle suspension is allowed to equilibrate in the freeze medium at room temperature for between about 15 minutes to about 60 minutes. The vials are then stored in a controlled-rate freeze chamber, such as ATCC ACS-6000, CoolCell LX, and the chamber is placed in a −70° C. (or colder) mechanical freezer for at least 24 hours. Alternately, a programmable freezer unit set is used to cool the cryovials at −1° C. per minute until a temperature of less than −70° C. is achieved. The vials are then transferred to a liquid nitrogen or −130° C. freezer. After 24 hours at −130° C., one cryovial is removed, the cells are cultured, and cell viability and sterility are determined.

What is claimed is:

1. Cell mimicking microparticles (CMMPs) consisting of the following:
   1. hyper compliant polymer particles (HCPPs) consisting of synthetic materials cross-linked with a cross-linker and having a mechanical compliance from 0.01 kPa to less than 10 kPa, the synthetic materials selected from the group consisting of a polyacrylamide, a poly(N-vinyl formamide), a polyethylene oxide, a dendrimer, a star polymer, a bioerodible polymer, a polydimethyl siloxane (PDMS), and a combination thereof;
   wherein the HCPPs comprise a predetermined size with a monodisperse diameter within a range of about 5 μm to about 40 μm, and including such that the HCPPs are each operative to encapsulate an agent; and,
   2. a coating on each of the HCPPs, with said coating including at least one material selected from the group consisting of a protein, a nucleotide sequence, a carbohydrate, a lipid, a cell plasma membrane, a therapeutic agent, a dye targeting agent, and a combination thereof;
   wherein the coating extends to the entirety of each of the HCPPs, and each HCPP is thereby entirely encased by coating.

2. The CMMPs according to claim 1 wherein the agent is in the form of a microparticle comprising a therapeutic agent or a nanoparticle comprising a therapeutic agent.

3. The CMMPs according to claim 2, wherein a viscoelasticity of the microparticle or the nanoparticle is distinct from a viscoelasticity of the HCPPs.

4. A method of calibrating a flow device for particle sizes in the range of cell sizes, the method comprising:
   preparing a fluid containing CMMPs of claim 1; and
   impelling the fluid through the flow device and measuring voltage as the HCPPs deform while flowing through the flow device thereby calibrating the flow device to a value accurate for cells.

5. The method according to claim 4, wherein the flow device is at least one selected from: a flow cytometer, a fluorescence-activated cell sorting (FACS) device, and a micro-fluidic device.

\* \* \* \* \*